(12) United States Patent
Kedrowski et al.

(10) Patent No.: US 11,357,811 B2
(45) Date of Patent: Jun. 14, 2022

(54) METHODS TO ISOLATE ANTI-MICROBIALS FROM FRUIT OR SEED EXTRACTS

(71) Applicant: WiSys Technology Foundation, Inc., Madison, WI (US)

(72) Inventors: Brant Lawrence Kedrowski, Oshkosh, WI (US); Teri Shors, Madison, WI (US)

(73) Assignee: WiSys Technology Foundation, Inc., Madison, WI (US)

( * ) Notice: Subject to any disclaimer, the term of this patent is extended or adjusted under 35 U.S.C. 154(b) by 182 days.

(21) Appl. No.: 15/211,966

(22) Filed: Jul. 15, 2016

(65) Prior Publication Data

US 2016/0324912 A1 Nov. 10, 2016

Related U.S. Application Data

(63) Continuation of application No. 13/918,070, filed on Jun. 14, 2013, now abandoned.

(60) Provisional application No. 61/660,332, filed on Jun. 15, 2012.

(51) Int. Cl.
*A61K 36/45* (2006.01)
*C07D 493/14* (2006.01)
*A61K 31/353* (2006.01)

(52) U.S. Cl.
CPC ............ *A61K 36/45* (2013.01); *A61K 31/353* (2013.01); *C07D 493/14* (2013.01); *A61K 2236/00* (2013.01)

(58) Field of Classification Search
CPC .................................................... A61K 36/45
See application file for complete search history.

(56) References Cited

U.S. PATENT DOCUMENTS

| | | | |
|---|---|---|---|
| 6,210,681 B1 * | 4/2001 | Walker ................... | A61K 36/45 424/732 |
| 6,608,102 B1 | 8/2003 | Howell et al. | |
| 2014/0004214 A1 | 1/2014 | Kedrowski et al. | |

FOREIGN PATENT DOCUMENTS

| CN | 1544423 A | * | 11/2004 |
|---|---|---|---|
| CN | 102086185 A | * | 6/2011 |

OTHER PUBLICATIONS

Lin et al. Agric Food Chem. Feb. 21, 2007; 55(4): 1084-1096 (Year: 2007).*
Erickson et al. Analytical Letters. vol. 14, Issue 11, abstract only. (Year: 1981).*
Kahkonen et al. J. Agric. Food Chem. 47, 3954-3962 (Year: 1999).*
J. Agric. Food Chem. 2004, 52, 2512-2517 (Year: 2004).*
Dolan et al. Journal of Chromatography A, vol. 910, Issue 2, Mar. 2, 2001, pp. 385 (Year: 2000).*
Qiao et al. J. Sep. Sci., 30, pp. 813-818. (Year: 2007).*
Foo et al. Phytochemistry 54. pp. 173-181. (Year: 2000).*
Su et al. Food Microbiology 27 (2010) 985-991. (Year: 2010).*
"U.S. Appl. No. 13/918,070, Advisory Action dated Oct. 19, 2015", 3 pgs.
"U.S. Appl. No. 13/918,070, Final Office Action dated Jun. 9, 2015", 9 pgs.
"U.S. Appl. No. 13/918,070, Non Final Office Action dated Jan. 15, 2016", 9 pgs.
"U.S. Appl. No. 13/918,070, Non Final Office Action dated Nov. 19, 2014", 12 pgs.
"U.S. Appl. No. 13/918,070, Response filed Feb. 19, 2015 to Non Final Office Action dated Nov. 19, 2014", 12 pgs.
"U.S. Appl. No. 13/918,070, Response filed Oct. 9, 2015 to Final Office Action dated Jun. 9, 2015", 8 pgs.
"U.S. Appl. No. 13/918,070, Response filed Oct. 22, 2014 to Restriction Requirement dated May 22, 2014", 6 pgs.
"U.S. Appl. No. 13/918,070, Restriction Requirement dated May 22, 2014", 10 pgs.
Kedrowski, Brant, "Exploring the Antiviral Potential of Wisconsin Cranberries", University of Wisconsin, Oshkosh, (2011), 13 pgs.
Kedrowski, Brant, "Isolation & Characterization of Antiviral Compounds From Commercial Cranberry Juice", University of Wisconsin, Oshkosh, (2010), 13 pgs.
Konowalchuk, J., et al., "Antiviral effect of commercial juices and beverages", Appl Environ Microbiol., 35(6), (Jun. 1978), 1219-20.
Lipson, S. M, et al., "Antiviral effects on bacteriophages and rotavirus by cranberry juice", Phytomedicine, 14(1), (Jan. 2007), 23-30.
Shmuely, H., et al., "Cranberry components for the therapy of infectious disease", Curr Opin Biotechnol., 23(2), (Apr. 2012), 148-52.
Titov, et al., Nature Chemical Biology, vol. 7, (2011), 182-188.
Weiss, E. I, et al., "Cranberry juice constituents affect influenza virus adhesion and infectivity", Antiviral Res., 66(1), (Apr. 2005), 9-12.

* cited by examiner

*Primary Examiner* — Amy L Clark

(74) *Attorney, Agent, or Firm* — Schwegman Lundberg & Woessner, P.A.

(57) ABSTRACT

The invention provides a method of isolating one or more compounds present in fruit juice or seed extracts that have anti-microbial activity.

12 Claims, 24 Drawing Sheets

| Dilution | CPE | | |
|---|---|---|---|
| | Test 1 | Test 2 | Test 3 |
| $10^{-4.5}$ | 4+, 4+, 4+, 4+ | 4+, 4+, 4+, 4+ | 4+, 4+, 4+, 4+ |
| $10^{-5.5}$ | 4+, 4+, 4+, 4+ | 4+, 4+, 4+, 4+ | 4+, 4+, 4+, 4+ |
| $10^{-6.5}$ | -, -, -, - | -, -, -, - | -, -, -, - |
| $10^{-7.5}$ | -, -, -, - | -, -, -, - | -, -, -, - |
| $10^{-8.5}$ | -, -, -, - | -, -, -, - | -, -, -, - |

Result: $10^{-4.5}$ Parainfluenza 3 = 100 TCID50, $10^{-5.5}$ Parainfluenza 3 = 10 TCID50

*FIG. 15A*

| F2a2 Concentration | CPE | | | | | |
|---|---|---|---|---|---|---|
| | 100 TCID50 Parainfluenza 3 | | | 10 TCID50 Parainfluenza 3 | | |
| | Test 1 | Test 2 | Test 3 | Test 1 | Test 2 | Test 3 |
| 100 µg/mL | -, -, -, - | -, -, -, - | -, -, -, - | -, -, -, - | -, -, -, - | -, -, -, - |
| 10 µg/mL | 4+, -, 4+, - | -, -, -, - | 4+, -, -, - | -, -, -, - | -, -, -, - | -, -, -, - |
| 1 µg/mL | 4+, 4+, 4+, 4+ | 4+, 4+, 4+, 4+ | 4+, 4+, 4+, 4+ | -, -, -, - | -, -, -, - | -, -, -, - |
| 100 ng/mL | 4+, 4+, 4+, 4+ | 4+, 4+, 4+, 4+ | 4+, -, 4+, 4+ | 2+, -, -, - | 1+, -, -, - | -, -, -, 1+ |

*FIG. 15B*

| F2a2 Concentration | % Inhibition | | | | | | | |
|---|---|---|---|---|---|---|---|---|
| | 100 TCID50 Parainfluenza 3 | | | | 10 TCID50 Parainfluenza 3 | | | |
| | Test 1 | Test 2 | Test 3 | Ave | Test 1 | Test 2 | Test 3 | Ave |
| 100 µg/mL | 100 | 100 | 100 | 100 | 100 | 100 | 100 | 100 |
| 10 µg/mL | 50 | 100 | 75 | 75 | 100 | 100 | 100 | 100 |
| 1 µg/mL | 0 | 0 | 0 | 0 | 100 | 100 | 100 | 100 |
| 100 ng/mL | 0 | 0 | 0 | 0 | 75 | 75 | 75 | 75 |

*FIG. 15C*

| F2a3 Concentration | CPE | | | | | |
|---|---|---|---|---|---|---|
| | 100 TCID50 Parainfluenza 3 | | | 10 TCID50 Parainfluenza 3 | | |
| | Test 1 | Test 2 | Test 3 | Test 1 | Test 2 | Test 3 |
| 100 µg/mL | -,-,-,- | -,-,-,- | -,-,-,- | -,-,-,- | -,-,-,- | -,-,-,- |
| 10 µg/mL | -,-,3+,4+ | 4+,-,4+,4+ | -,-,4+,- | -,-,-,- | -,-,-,- | -,-,-,- |
| 1 µg/mL | 4+,4+,4+,4+ | 4+,4+,4+,4+ | 4+,4+,4+,4+ | -,-,-,- | -,-,-,- | -,-,4+,- |
| 100 ng/mL | 4+,4+,4+,4+ | 4+,4+,4+,4+ | 4+,-,4+,4+ | -,-,-,- | -,-,2+,- | 4+,-,4+,4+ |

*FIG. 15D*

| F2a3 Concentration | % Inhibition | | | | | | | |
|---|---|---|---|---|---|---|---|---|
| | 100 TCID50 Parainfluenza 3 | | | | 10 TCID50 Parainfluenza 3 | | | |
| | Test 1 | Test 2 | Test 3 | Ave | Test 1 | Test 2 | Test 3 | Ave |
| 100 µg/mL | 100 | 100 | 100 | 100 | 100 | 100 | 100 | 100 |
| 10 µg/mL | 50 | 25 | 25 | 34 | 100 | 100 | 100 | 100 |
| 1 µg/mL | 0 | 0 | 0 | 0 | 100 | 100 | 25 | 75 |
| 100 ng/mL | 0 | 0 | 0 | 0 | 100 | 75 | 0 | 58 |

*FIG. 15E*

| F2a2 Concentration | % Inhibition | | | | | | | |
|---|---|---|---|---|---|---|---|---|
| | 100 TCID50 Parainfluenza 3 | | | | 10 TCID50 Parainfluenza 3 | | | |
| | Test 1 | Test 2 | Test 3 | Ave | Test 1 | Test 2 | Test 3 | Ave |
| 100 mg/L | 100 | 100 | 100 | 100 | 100 | 100 | 100 | 100 |
| 10 mg/L | 50 | 100 | 75 | 75 | 100 | 100 | 100 | 100 |
| 1 mg/L | 0 | 0 | 0 | 0 | 100 | 100 | 100 | 100 |
| 0.1 mg/L | 0 | 0 | 0 | 0 | 75 | 75 | 75 | 75 |

*FIG. 15F*

| F2a3 Concentration | % Inhibition | | | | | | | |
|---|---|---|---|---|---|---|---|---|
| | 100 TCID50 Parainfluenza 3 | | | | 10 TCID50 Parainfluenza 3 | | | |
| | Test 1 | Test 2 | Test 3 | Ave | Test 1 | Test 2 | Test 3 | Ave |
| 100 mg/L | 100 | 100 | 100 | 100 | 100 | 100 | 100 | 100 |
| 10 mg/L | 50 | 25 | 25 | 34 | 100 | 100 | 100 | 100 |
| 1 mg/L | 0 | 0 | 0 | 0 | 100 | 100 | 25 | 75 |
| 0.1 mg/L | 0 | 0 | 0 | 0 | 100 | 75 | 0 | 58 |

*FIG. 15G*

| F2a2 Concentration | % Inhibition | | | | | | | |
|---|---|---|---|---|---|---|---|---|
| | 100 TCID50 Influenza A/H3N2 | | | | 10 TCID50 Influenza A/H3N2 | | | |
| | Test 1 | Test 2 | Test 3 | Ave | Test 1 | Test 2 | Test 3 | Ave |
| 100 mg/L | 100 | 100 | 100 | 100 | 100 | 100 | 100 | 100 |
| 10 mg/L | 0 | 50 | 50 | 33 | 100 | 100 | 100 | 100 |
| 1 mg/L | 0 | 0 | 0 | 0 | 50 | 50 | 50 | 50 |
| 0.1 mg/L | 0 | 0 | 0 | 0 | 0 | 0 | 0 | 0 |
FIG. 16A
| F2a3 Concentration | % Inhibition | | | | | | | |
|---|---|---|---|---|---|---|---|---|
| | 100 TCID50 Influenza A/H3N2 | | | | 10 TCID50 Influenza A/H3N2 | | | |
| | Test 1 | Test 2 | Test 3 | Ave | Test 1 | Test 2 | Test 3 | Ave |
| 100 mg/L | 100 | 100 | 100 | 100 | 100 | 100 | 100 | 100 |
| 10 mg/L | 0 | 0 | 0 | 0 | 50 | 100 | 50 | 67 |
| 1 mg/L | 0 | 0 | 0 | 0 | 50 | 0 | 0 | 17 |
| 0.1 mg/L | 0 | 0 | 0 | 0 | 0 | 0 | 0 | 0 |
FIG. 16B
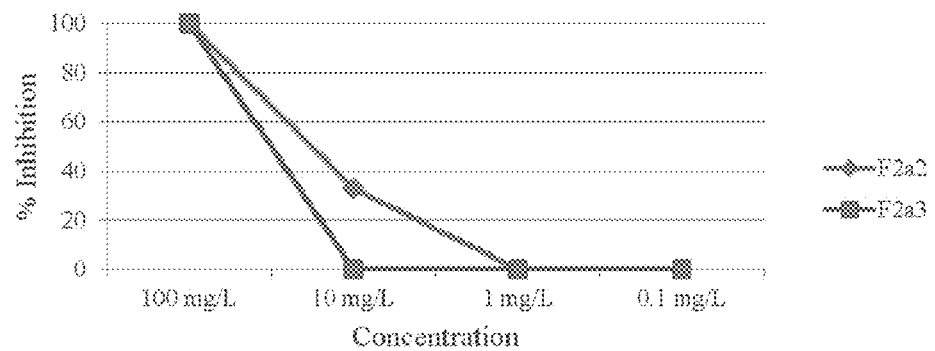
FIG. 16C
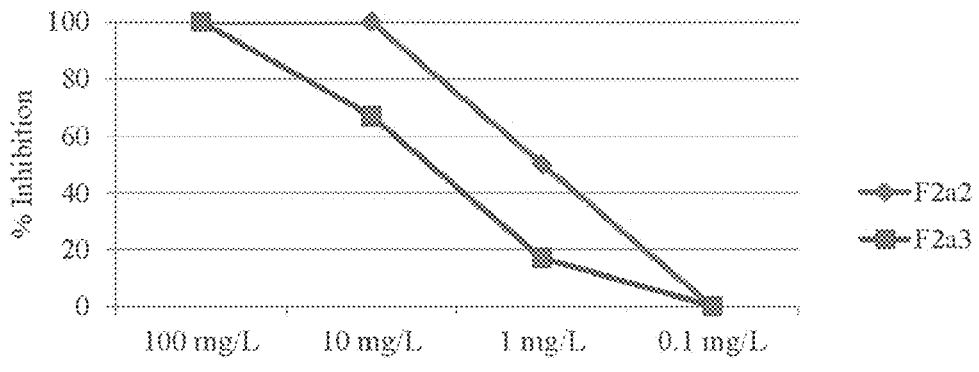
FIG. 16D retention time = 4.67 min
molecular formula = $C_{20}H_{24}O_6$
molecular weight = 360.40 amu
name = triptolide retention time = 3.97 min
molecular formula = $C_{11}H_{12}O_5$
molecular weight = 224.07 amu
name = sinapinic acid retention time = 3.38 min
molecular formula = $C_{21}H_{20}O_{13}$
molecular weight = 480.38 amu
name = myricetin-3-galactoside

| % Inhibition of Influenza A/H1N1 | | | | | | |
|---|---|---|---|---|---|---|
| Sample | 100 TCID 50 | | | 10 TCID 50 | | |
| BLK4-124 H2O | Test 1 | Test 2 | Ave | Test 1 | Test 2 | Ave |
| 100 mg/L | 50 | 50 | 50 | 50 | 0 | 25 |
| 10 mg/L | 0 | 0 | 0 | 0 | 0 | 0 |
| 1 mg/L | 0 | 0 | 0 | 0 | 0 | 0 |
| 0.1 mg/L | 0 | 0 | 0 | 0 | 0 | 0 |
| Sample | 100 TCID 50 | | | 10 TCID 50 | | |
| BLK4-124 EtOH | Test 1 | Test 2 | Ave | Test 1 | Test 2 | Ave |
| 100 mg/L | 100 | 100 | 100 | 100 | 100 | 100 |
| 10 mg/L | 100 | 100 | 100 | 100 | 100 | 100 |
| 1 mg/L | 0 | 0 | 0 | 100 | 0 | 50 |
| 0.1 mg/L | 0 | 0 | 0 | 0 | 0 | 0 |
| Sample | 100 TCID 50 | | | 10 TCID 50 | | |
| BLK4-124 MeOH | Test 1 | Test 2 | Ave | Test 1 | Test 2 | Ave |
| 100 mg/L | 100 | 100 | 100 | 100 | 100 | 100 |
| 10 mg/L | 100 | 100 | 100 | 100 | 100 | 100 |
| 1 mg/L | 100 | 100 | 100 | 100 | 100 | 100 |
| 0.1 mg/L | 0 | 0 | 0 | 100 | 100 | 100 |
| Sample | 100 TCID 50 | | | 10 TCID 50 | | |
| BLK4-124 i-PrOH/H2O | Test 1 | Test 2 | Ave | Test 1 | Test 2 | Ave |
| 100 mg/L | 100 | 100 | 100 | 100 | 100 | 100 |
| 10 mg/L | 50 | 50 | 50 | 0 | 50 | 25 |
| 1 mg/L | 0 | 0 | 0 | 0 | 0 | 0 |
| 0.1 mg/L | 0 | 0 | 0 | 0 | 0 | 0 |
| Sample | 100 TCID 50 | | | 10 TCID 50 | | |
| BLK4-124 n-PrOH/H2O | Test 1 | Test 2 | Ave | Test 1 | Test 2 | Ave |
| 100 mg/L | 0 | 0 | 0 | 0 | 0 | 0 |
| 10 mg/L | 0 | 0 | 0 | 0 | 0 | 0 |
| 1 mg/L | 0 | 0 | 0 | 0 | 0 | 0 |
| 0.1 mg/L | 0 | 0 | 0 | 0 | 0 | 0 |
| Sample | 100 TCID 50 | | | 10 TCID 50 | | |
| JAM1-91 | Test 1 | Test 2 | Ave | Test 1 | Test 2 | Ave |
| 100 mg/L | 0 | 0 | 0 | 0 | 0 | 0 |
| 10 mg/L | 0 | 0 | 0 | 0 | 0 | 0 |
| 1 mg/L | 0 | 0 | 0 | 0 | 0 | 0 |
| 0.1 mg/L | 0 | 0 | 0 | 0 | 0 | 0 |

*FIG. 21B*

METHODS TO ISOLATE ANTI-MICROBIALS FROM FRUIT OR SEED EXTRACTS

CROSS-REFERENCE TO RELATED APPLICATIONS

This application is a Divisional of U.S. application Ser. No. 13/918,070, filed Jun. 14, 2013, which application claims the benefit of the filing date under 35 U.S.C. § 119(e) of U.S. application Ser. No. 61/660,332, filed Jun. 15, 2012, the disclosure of which are incorporated by reference herein.

BACKGROUND

Cranberries are rich in phytonutrients including polyphenols and have among the highest antioxidant content of any food. Numerous health benefits have been associated with cranberry consumption, e.g., anti-bacterial properties, especially for preventing urinary tract infections, anti-aging properties, anti-cancer properties, anti-ulcer properties, dental-related benefits, and heart-related benefits. There are also a few reports of anti-viral properties (Konowalchuck et al., *Appl. and Environ. Microbiol.*, 35:1219 (1978); Weiss et al., *Antiviral Res.*, 66:9 (2005), Lipson et al., *Phytomedicine*, 14:23 (2007); and Shors et al., 24$^{th}$ Annual American Soc. For Virology Meeting (2005). However, the compound(s) associated with those properties have yet to be identified.

SUMMARY OF THE INVENTION

The invention provides a method to identify compounds in fruit or fruit seed extracts, such as cranberry extracts, that have anti-microbial activity. The method includes subjecting extracts, e.g., fruit extracts including fruit juice and seed extracts or reconstituted fruit extracts or juice such as those from cranberries, raspberries or grapes, to one or more separation techniques, identifying and isolating subtractions with anti-microbial activity and optionally repeating separation and identification/isolation steps using different parameters, prior to isolating fractions having a plurality of individual compounds, or substantially pure fractions having individual chemical compounds, responsible for anti-microbial, e.g., anti-viral, activity. Generally, a "substantially pure" composition will comprise more than about 80% of a single macromolecular species present in the composition, e.g., more than about 85%, about 90%, about 95%, and about 99%, and in one embodiment, the object species is purified to essential homogeneity (contaminant species cannot be detected in the composition by conventional detection methods) wherein the composition consists essentially of a single macromolecular species. In one embodiment, a substantially pure fraction is one where a single compound represents at least 95% all macromolecular species present in the composition. In one embodiment, an isolated fraction is one where a single (first) compound represents at least 50%, or at least 60%, 70%, 80%, 90%, or any integer between 60 and 100, of all macromolecular species in the fraction but other compounds in the fraction individually or in combination with the first compound provide for anti-microbial activity. In one embodiment, chromatographic methods were used to separate the multitude of compounds present in cranberry extracts into several fractions, each containing a simpler mixture of compounds. For example, high performance liquid chromatography (HPLC) and/or solid phase extraction (SPE) were used to separate these complex mixtures. In one embodiment, simulated moving bed chromatography (SMBC) may be employed to separate mixtures. Thus, one type of separation method may be employed once, or two or more different types of separation methods may be employed in succession. In one embodiment, one type of chromatography column may be employed individually or in tandem, or two or more different types of columns may be employed sequentially or in tandem. In one embodiment, to detect activity, biological assays are employed, e.g., assays that include one or more different viruses, e.g., vaccinia virus (a poxvirus), human parainfluenza virus type 3 (PIV3), influenza A virus (e.g., H1N1 and H2N3 strains) and/or poliovirus (e.g., Sabin Strain, Sero Type 1), one or more different bacterial strains or species, and/or one or more different fungi, to focus further separation on active fractions. Through this iterative approach of bioassay-guided chemical separations, the complex mixture of compounds in cranberries was narrowed down to one or a few substantially pure compounds. Once separated as those pure substances, analytical methods were used to elucidate the chemical structures of these substances. The compounds displaying signs of anti-microbial activity may then be purified in larger quantities, e.g., using the methods to identify those compounds which may include eliminating one or more steps, or through SMBC technology, and the resulting compositions may be employed as a nutraceutical or a pharmaceutical in compositions, e.g., in powdered, tablet or liquid formulations.

As described herein below, the compounds myricetin-beta-3-galactoside, sinapinic acid, triptolide, and members of the proanthocyanidin class were isolated from Ocean Spray 90MX spray-dried cranberry powder through a separation sequence that included filtration, solid phase extraction, ion exchange chromatography, and HPLC. The structure of the compounds was determined using proton nuclear magnetic resonance spectroscopy ($^1$H NMR), MALDI-TOF mass spectrometry, Ultra High Performance Liquid Chromatography (UPLC)-Quadrupole/Time of Flight (Q-TOF) mass spectrometry, and/or ultraviolet (UV) spectroscopy. Thus, fractions having myricetin-beta-3-galactoside, sinapinic acid, triptolide, type A proanthocyanidin compounds, or combinations thereof, may be employed as anti-microbials.

Thus, the invention provides a compound of formula (I), e.g., myricetin-beta-3-galactoside, isolated from fruit or seed extracts, as well as compositions having that compound, for use in prophylactic or therapeutic methods. In one embodiment, a compound of formula (I) has the following structure:

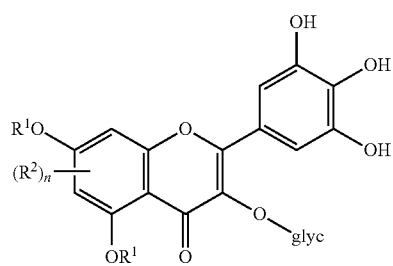

Wherein each $R^1$ is independently selected from the group consisting of H, $(C_1-C_6)$alkyl, and $(C_1-C_6)$alkanoyl; each $R^2$ is independently selected from the group consisting of halo, cyano, nitro, $(C_1-C_6)$alkyl, $(C_1-C_6)$alkoxyl, $(C_1-C_6)$alkanoyl, $(C_1-C_6)$alkanoyloxy, and $(C_1-C_6)$alkylcarboxamido; n=0, 1, or 2; glyc is a glycoside unit selected from the group consisting of a monosaccharide, a disaccharide, and a polysaccharide having about three to about six monosaccharide units, wherein the glycoside can be unsubstituted, or can comprise one or more acyl groups, one or more halo groups, one or more carboxylic acid groups, one or more carboxyester acid ester groups, or one or more carboxamido groups. In one embodiment, both $R^1$ groups are hydrogen. In one embodiment, n=0. In one embodiment, glyc is a monosaccharide unit. In one embodiment, glyc is a disaccharide unit. In one embodiment, glyc is a galactoside. In one embodiment, glyc is a β-galactoside.

The invention also provides a compound of formula (II), e.g., sinapinic acid, isolated from fruit or seed extracts, as well as compositions having that compound, for use in prophylactic or therapeutic methods. A compound of formula (II) has the following structure:

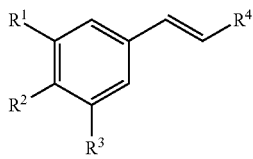

wherein each of $R^1$, $R^2$, and $R^3$ is independently selected from the group consisting of hydroxyl and $(C_1-C_6)$alkoxyl, $R^4$ is $CO_2H$, $CO_2M$ wherein M is a cation, or is $CO_2(C_1-C_6)$alkyl.

Further provided is a compound of formula (III), e.g., triptolide, isolated from fruit or seed extracts, as well as compositions having that compound, for use in prophylactic or therapeutic methods. A compound of formula (III) has the following structure:

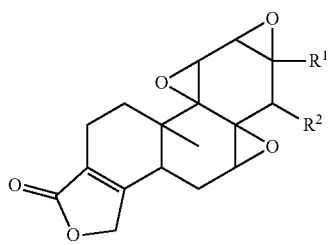

wherein $R^1$ is H, $(C_1-C_6)$ alkyl or $(C_1-C_6)$alkoxyl; $R^2$ is H, OH, $(C_1-C_6)$alkoxyl, or $O(CH_2)_nOR^3$, wherein n=1, 2, or 3, and $R^3$ is H, $(C_1-C_6)$alkyl, $(C_1-C_6)$acyl, $-(CH_2)_mCO_2H$ wherein m=1, 2, or 3, or $-P(O)(OH)_2$, or a salt thereof.

Also provided is a compound of formula (IV), e.g., a proanthocyanidin, isolated from fruit or seed extracts, as well as compositions having that compound, for use in prophylactic or therapeutic methods. A compound of formula (IV) has the following structure:

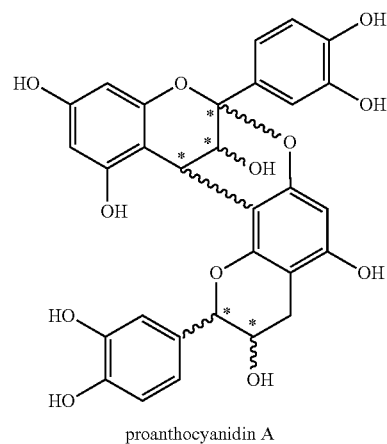 [SMILES: Oc1cc(O)c2c(c1)OC1(c3ccc(O)c(O)c3)Oc3cc(O)c4c(c3C2C1O)OC(c1ccc(O)c(O)c1)C(O)C4]

proanthocyanidin A wherein * is a stereogenic carbon atom. Each stereogenic atom may be of either (R)- or (S)-configuration.

In one embodiment, the invention provides a composition comprising a substantially pure preparation of compound of formula (I), (II), (III), or (IV), or a combination thereof and optionally a pharmaceutically acceptable carrier. In one embodiment, the composition is in oral dosage form. In one embodiment, the composition comprises two or more distinct compounds having formula (IV). In one embodiment, the composition comprises two or more distinct compounds selected from formula (I), (II) or (III).

In one embodiment, the invention provides a composition comprising an isolated fraction of a fruit or fruit seed extract having a compound of formula (I), (II), (III), or (IV), or a combination thereof, and optionally a pharmaceutically acceptable carrier. In one embodiment, the composition is in oral dosage form. In one embodiment, the composition comprises two or more distinct compounds having formula (IV). In one embodiment, the composition comprises two or more distinct compounds selected from formula (I), (II) or (III).

In one embodiment a composition useful in the prophylactic or therapeutic methods of the invention, is prepared by the separation and isolation methods of invention, which yield a separated and isolated fraction of a fruit or fruit seed extracts that has anti-microbial activity and is characterized by the presence of one or more of the following; myricetin-beta-3-galactoside, sinapinic acid, triptolide, proanthocyanidin A, e.g., where one or more of those compounds represents at least 50% of the population of compounds in the preparation.

The compositions may be in dry (e.g., powder or crystal) form, or in liquid form, e.g., dissolved in an aqueous liquid, such as those suitable for consumption or administration.

Further provided is a method to prevent, inhibit or treat a microbial infection in an animal, e.g., an avian or mammal. The method includes administering a composition that includes one or more of proanthocyanin, or one or more of a flavonol, diterpenoid epoxide, or phenylpropanoid, e.g., a hydroxycinnamic acid, or combinations thereof, to the animal in an effective amount. In one embodiment, the compound in the composition prevents or inhibits microbial infection and/or eliminates or inhibits microbial growth, e.g., replication. In one embodiment, the mammal is human. In one embodiment, the composition is orally or intravenously administered. In one embodiment, the composition is a tablet. In one embodiment, the microbe is a virus, e.g., a poxvirus or an influenza virus.

BRIEF DESCRIPTION OF THE FIGURES

FIGS. 3-6 show the progression of purification of compounds F2a2 and F2a3 from 90MX cranberry powder at each stage by HPLC. The column used for analytical HPLC was a Waters Symmetry brand C8 column, 3.9×150 mm, with a 5 µm particle size and a flow rate 0.5 mL/min. A binary solvent gradient was used for these analytical HPLC separations with solvent A=water+0.1% formic acid and solvent B=methanol+0.1% formic acid. Solvent composition at various times was as follows, time (percent B): initial (10% B), 50 min. (35% B), 80 min. (60% B), 85 min. (80% B), 90 min. (80% B).

FIG. 3. Overlaid HPLC chromatograms are shown of the initial separation of 90MX into fractions F1, F2, and F3 by C18 solid phase extraction. The column contained C18 media from Grace-Davison Discovery Sciences, using an Octave 100 chromatograph (Semba Biosciences, Middleton, Wis.).

FIG. 4. Overlaid HPLC chromatograms are shown before and after the second purification step using strong cation exchange chromatography. The column was a Redi-Sep Rf SCX brand, 5 g, from Isco/Teledyne. Both traces were recorded over a range of wavelengths from 250 to 600 nm. The red trace shows the starting F2 material while the green trace shows the purified F2a material.

FIG. 5. Overlaid HPLC chromatograms are shown of fractions F2a2, F2a3, F2a4, and F2a5 separated in the third step by prep-scale C8 HPLC. A Waters Symmetry C8 column was used for prep HPLC, 19×150 mm, 7 µm, with a flow rate of 12 mL/min. The same solvent program as was used in C8 analytical HPLC was used for prep HPLC. All traces in FIG. 5 were recorded over a range of wavelengths from 250 to 600 nm.

FIG. 12. A vaccinia virus plaque reduction assay is shown. Methods were adapted from *Current Protocols in Molecular Biology* (1998), Unit 16.16 contributed by Bernard Moss and Patricia L. Earl. The titer of the vaccinia virus stock was determined by plaque assay prior to the inhibition assay. Virus was added to each sample dilution and the 1% DMSO control to yield between 20 and 80 plaque-forming units (PFU) of vaccinia virus. Each sample dilution plus virus was inoculated into duplicate wells of a 12-well plate containing BS-C-1 cells. Each sample dilution without virus was inoculated to a single well to test for cytotoxicity. Four wells were inoculated with virus only to confirm the virus concentration of the working dilution of vaccinia virus at the time of the test. The plates were incubated for 45 minutes at 37° C. with 5% $CO_2$. The medium was aspirated from each well and 1 mL of EMEM5 growth medium was added to each well. The plates were incubated for two days at 37° C. with 5% $CO_2$. The plates were stained with 0.25% crystal violet in 20% ethanol and the plaques were counted. An example of this testing protocol is shown in FIG. 10. In this test, healthy BS-C-1 cells take up the stain and appear purple while cells killed by vaccinia infection appear as colorless spots (plaques). Counting the number of plaques present in each test well (right sample plate) compared to control wells (left plate) provides a measure of viral inhibition for juice samples.

FIG. 13 shows an example of a poliovirus 1 inhibition assay. Methods were adapted form The World Health Organizations *Polio Laboratory Manual* 4th edition (2004). Poliovirus 1 did not show good plaque formation in BS-C-1 cells when tested by plaque reduction assay as described for the vaccinia virus. The procedures were developed to use neutralization testing with cranberry extracts in place of poliovirus antiserum. The $TCID_{50}$ titer of the Poliovirus 1 stock was determined prior to the inhibition assay. Virus was added to each sample dilution and the 1% DMSO control to yield concentrations of 100 $TCID_{50}$ and 10 $TCID_{50}$ of poliovirus 1. Each sample dilution plus virus was inoculated into four wells of a 24-well plate containing BS-C-1 cells. Each sample dilution without virus was inoculated to a single well to test for cytotoxicity. A back titer was performed to confirm the virus concentration of the working dilution to be 100 $TCID_{50}$ of poliovirus 1 at the time of the test. The plates were incubated for one hour at 37° C. with 5% $CO_2$. The medium was aspirated from each well and 1 mL of EMEM5 growth medium was added to each well. The plates were incubated for seven days at 37° C. with 5% $CO_2$ with the medium being replaced on day three or four. The plates were stained with 0.25% crystal violet in 20% ethanol. The left plate shows back titer results for poliovirus at varying concentrations of virus after staining. Wells containing healthy BS-C-1 cells stain purple while those exhibiting a cytopathic effect appear colorless. The test plate at right shows inhibition at sample concentrations greater than or equal to 1 mg/mL.

Figure 14:
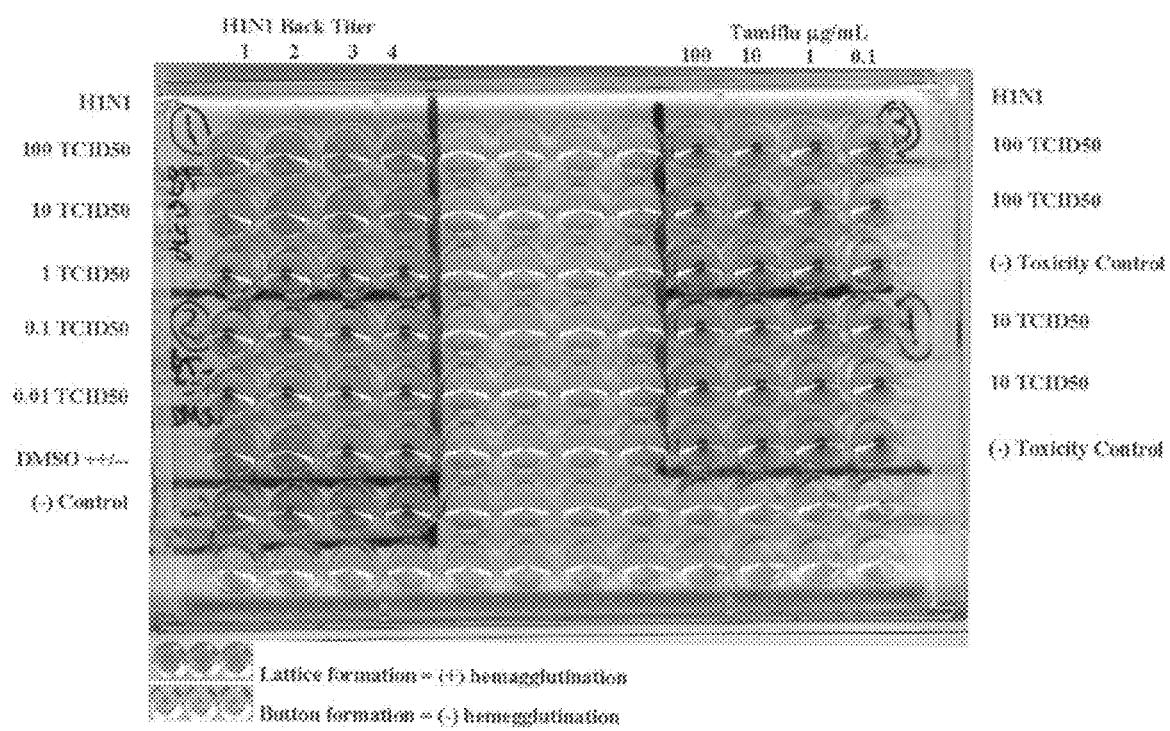
Figure 15H:
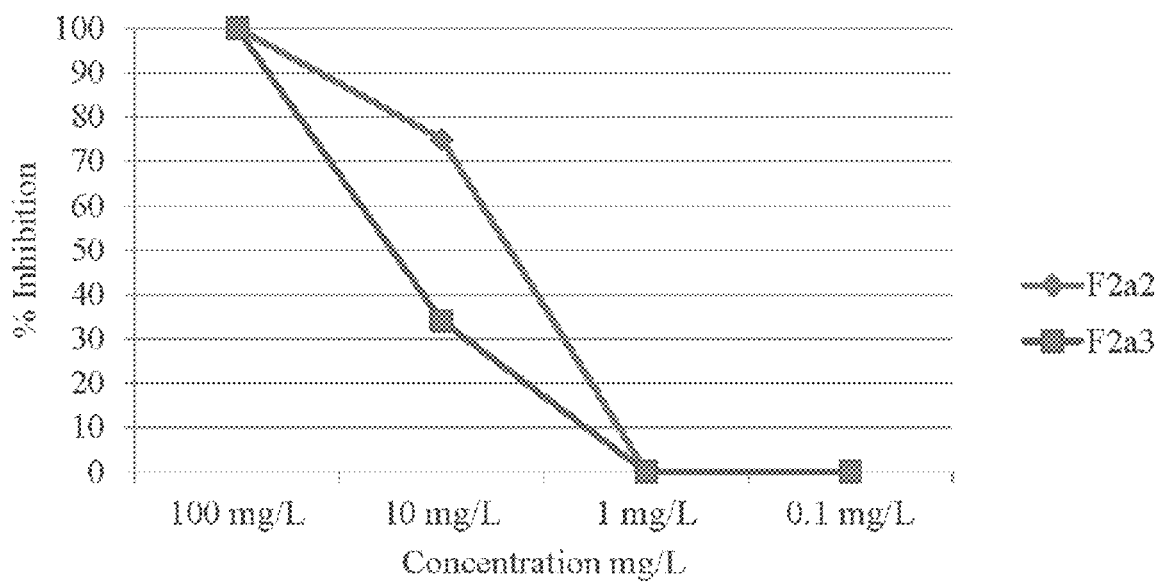
Figure 15I:
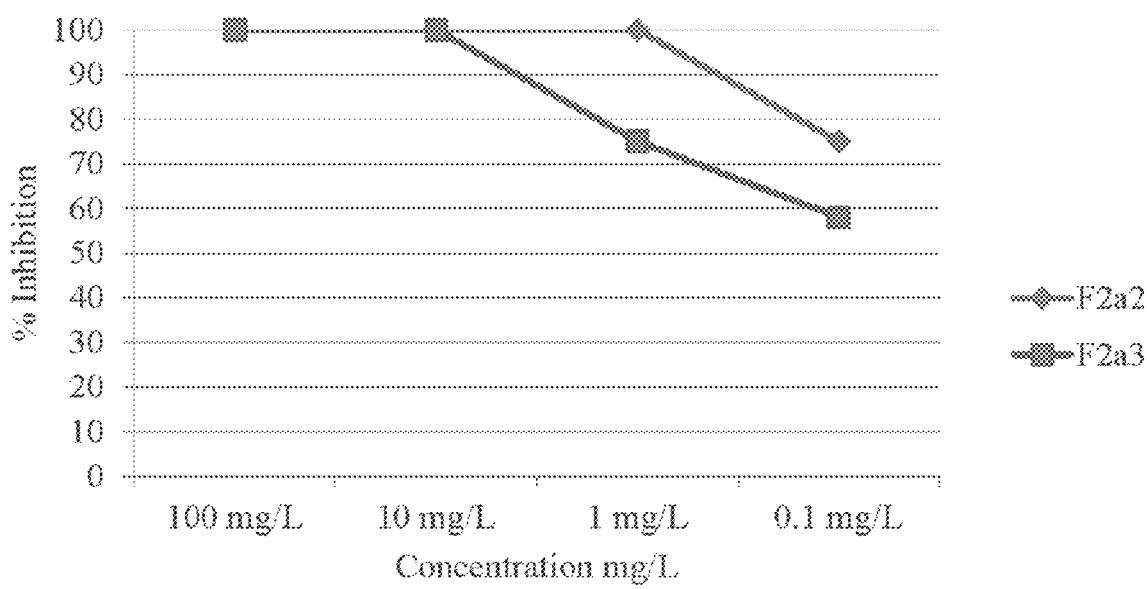

FIG. 14 shows an example of an influenza A/H1N1 inhibition assay using the known inhibitor Tamiflu. Methods were adapted from the World Health Organizations Global Influenza Surveillance Network's *Manual for the Laboratory Diagnosis and Urological Surveillance of Influenza* (2011). Influenza A viruses do not form plaques in MDCK cells and may not show cytopathic effect even when the cells are infected. The methods were developed to use cranberry extracts as viral inhibitor in place of influenza-specific antiserum. Therefore, inhibition of viral cytopathic effect (CPE) and detection of the presence of virus by hemagglutination (HA) were tested. The $TCID_{50}$ of the influenza A/H1N1 stock virus was determined prior to the inhibition assay. Virus was added to each sample dilution to yield concentrations of 100 $TCID_{50}$ and 10 $TCID_{50}$ of influenza A/H1N1 Each sample dilution plus virus was inoculated into duplicate wells of a 12-well plate containing MDCK cells. Each sample dilution without virus was inoculated to a single well to test, for cytotoxicity. A back titer was performed to confirm the virus concentration of the working dilution to be 100 $TCID_{50}$ of influenza A/H1N1 at the time of the test. The plates were incubated for one hour at 34° C. with 5% $CO_2$. The medium was aspirated from each well and replaced with 1 mL of EMEM5 growth medium. The plates were incubated for five days at 34° C. with 5% $CO_2$ with the medium being replaced on day three or four. The plates were observed microscopically for CPE. Influenza infection was confirmed by testing samples from each well for hemagglutination of guinea pig red blood cells in 96-well V-bottom plates. The presence of influenza virus wall cause the formation of a lattice with a suspension of 0.75% guinea pig red blood cells in 1×PBS with 0.4% bovine serum albumin. This is referred to as hemagglutination. Wells in winch the virus has been inhibited will have no hemagglutination and the red blood cells will settle to the bottom forming a red button. The left portion of the plate shows back titer results for H1N1. The right portion shows test results with a known inhibitor of influenza, the antiviral drug Tamiflu. Red buttons in each test well indicate effective viral inhibition.

FIGS. 15A-I show results for anti-PIV3 activity of fractions F2a2 and F2a3. A) Back titers results. B-C) CPE and percent inhibition with F2a2. D-E) CPE and percent inhibition with F2a3. F-G) Percent inhibition with 100 $TCID_{50}$ of PIV3. H-I) Percent inhibition with 10 $TCID_{50}$ of PIV3.

FIGS. 16A-D show results for anti-influenza virus activity of fractions F2a2 and F2a3. A-B) Table with percent inhibition by F2a2 or F2a3 with 100 $TCID_{50}$ of H3N2. C-D) Graph of percent inhibition by F2a2 or F2a3 with 10 $TCID_{50}$ of H3N2.

FIGS. 17A-17F. Analysis of fraction F2a2. A-C) UPLC chromatograms of major components in F2a2. D-F) UPLC chromatograms of minor components in F2a2. G) Structures for molecules (or related compounds) corresponding to the major components.

FIGS. 18A-18G. Analysis of fraction F2a3. A-C) UPLC chromatograms of major components in F2a3. D-F) UPLC chromatograms of minor components in F2a3. G) Structures consistent with major components.

Figure 19A:
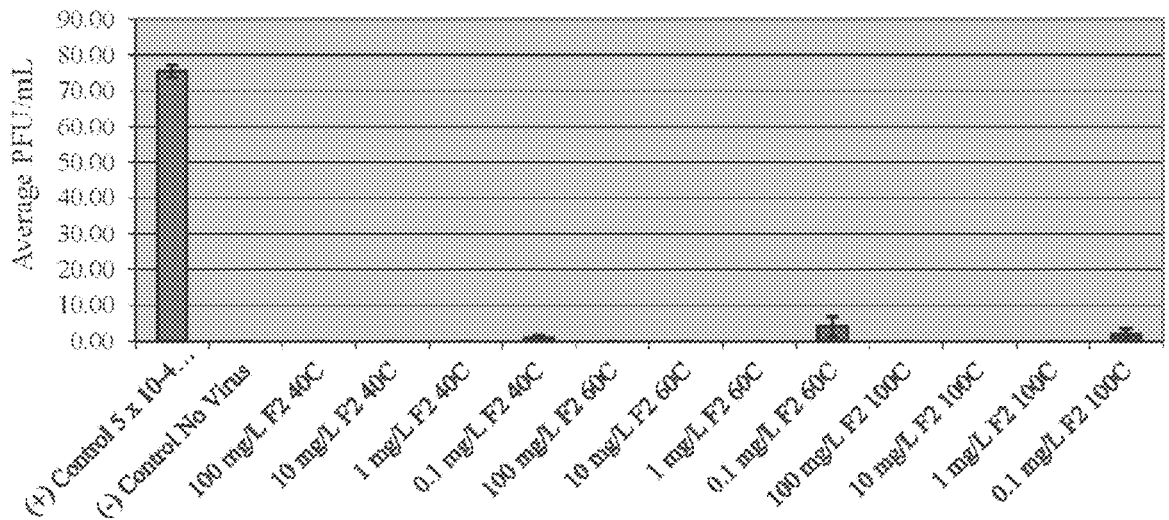
Figure 19B:
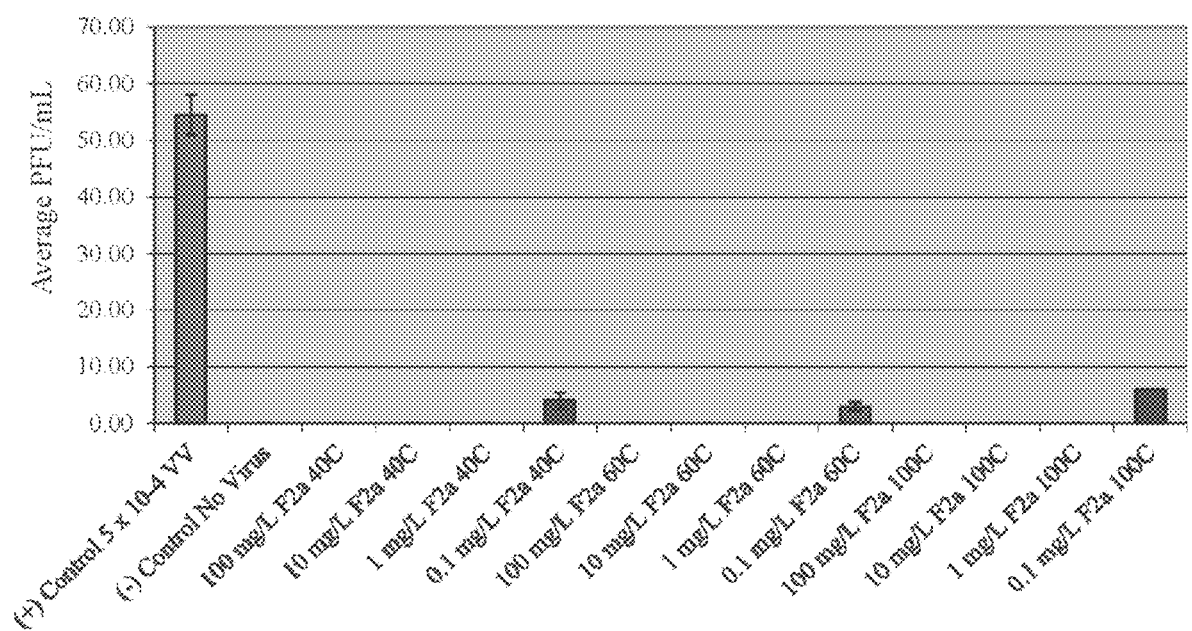

FIGS. 19A-19B. Temperature stability study of F2 (panel A) and F2a2 (panel B).

Figure 20A:
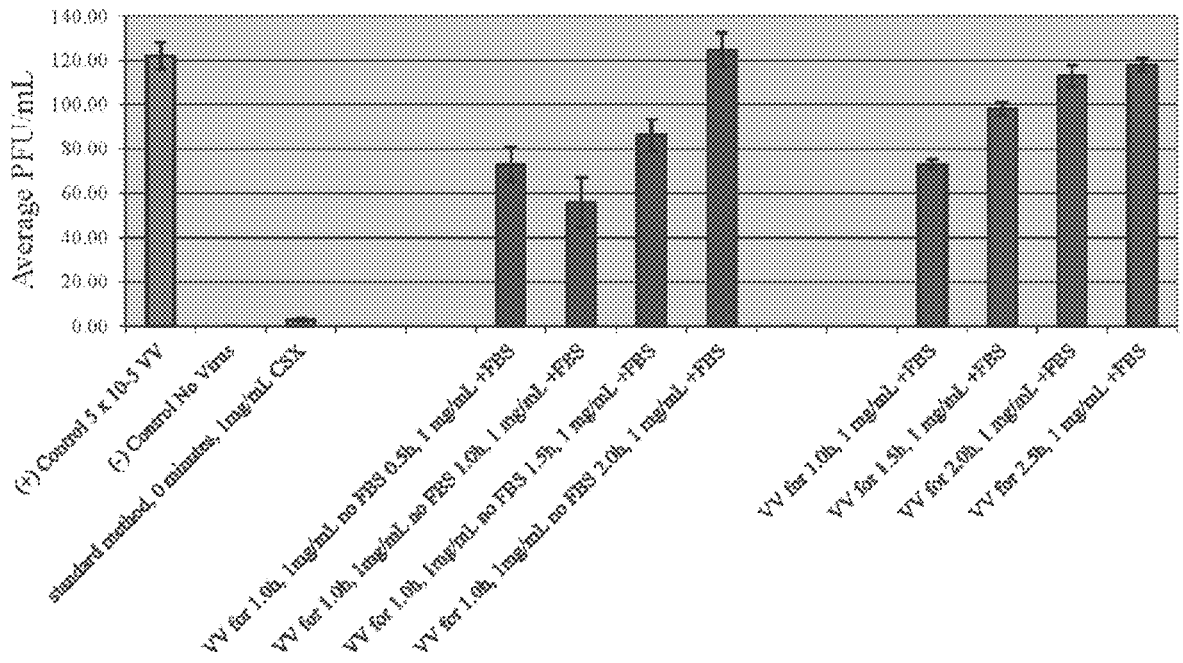
Figure 20B:
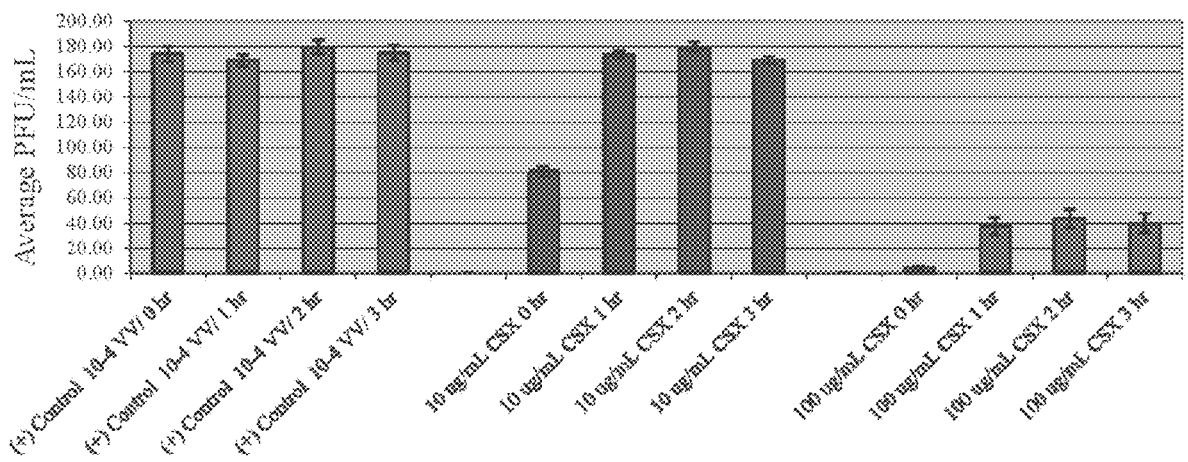

FIGS. 20A-20B. Anti-viral activity of cranberry seed powder when applied subsequent to (panel A) or before (panel B) vaccinia virus infection.

FIGS. 21A-21D. Comparison of anti-viral activity (panel A, vaccinia virus; panels B-D, influenza virus) of cranberry seed powder prepared by different methods. Material labeled as JAM or JAM1-91 refers to cranberry seed powder extracts produced by extraction using 70% methanol/30% water.

DETAILED DESCRIPTION

Cranberry juice is an enormously complex mixture containing hundreds of compounds in varying amounts. In order to study the anti-microbial effects of cranberries or other fruits, the bioactive agents in juices or extracts thereof are isolated in sufficient quantities to permit chemical characterization and anti-microbial testing. In one embodiment, this separation is accomplished using chromatographic techniques including but not limited to Solid Phase Extraction (SPE) and preparatory-scale High Performance Liquid Chromatography (HPLC), either alone or in combination, e.g., sequentially.

Exemplary Separation Methods

Solid-phase extraction (SPE) is a separation process by which compounds that are dissolved or suspended in a liquid mixture are separated from other compounds in the mixture according to their physical and chemical properties. Analytical laboratories use SPE to concentrate and purify samples for analysis. SPE uses the affinity of solutes dissolved or suspended in a liquid (known as the mobile phase) for a solid through which the sample is passed (known as the stationary phase) to separate a mixture into desired and undesired components. The result is that either the desired analytes of interest or undesired impurities in the sample are retained on the stationary phase. The portion that passes through the stationary phase is collected or discarded, depending on whether it contains the desired analytes or undesired impurities. If the portion retained on the stationary phase includes the desired analytes, they can then be removed from the stationary phase for collection in an additional step, in which the stationary phase is rinsed with an appropriate eluent. The stationary phase comes in the form of, for example, a packed syringe-shaped cartridge, a 96 well plate, a 47- or 90-mm flat disk, or a MEPS device, each of winch can be mounted on its specific type of extraction manifold. The manifold allows multiple samples to be processed by holding several SPE media in place and allowing for an equal number of samples to pass through them simultaneously. A typical cartridge SPE manifold can accommodate up to 24 cartridges, while a typical disk SPE manifold can accommodate 6 disks. Most SPE manifolds are equipped with a vacuum port. Application of vacuum speeds up the extraction process by pulling the liquid sample through the stationary phase. The analytes are collected in sample tubes inside or below the manifold after they pass through the stationary phase. Solid phase extraction cartridges and disks are available with a variety of stationary phases, each of which can separate analytes according to different chemical properties. Most stationary phases are based on silica that has been bonded to a specific functional group. Some of these functional groups include hydrocarbon chains of variable length (for reversed phase SPE), quaternary ammonium or amino groups (for anion exchange), and sulfonic acid or carboxyl groups (for cation exchange).

Normal Phase SPE Procedure

A typical solid phase extraction involves four basic steps. First, the cartridge is equilibrated with a non-polar solvent or slightly polar, which wets the surface and penetrates the bonded phase. Then water, or buffer of the same composition as the sample, is typically washed through the column to wet the silica surface. The sample is then added to the cartridge. As the sample passes through the stationary phase, the analytes in the sample will interact and retain on the sorbent while the solvent, salts, and other impurities pass through the cartridge. After the sample is loaded, the cartridge is washed with buffer or solvent to remove further impurities. Then, the analyte is eluted with a non-polar solvent or a buffer of the appropriate pH.

Reversed Phase SPE

Reversed phase SPE separates analytes based on their polarity. The stationary phase of a reversed phase SPE cartridge is derivatized with hydrocarbon chains, which retain compounds of mid to low polarity due to the hydrophobic effect. The analyte can be eluted by washing the cartridge with a non-polar solvent, which disrupts the interaction of the analyte and the stationary phase.

Ion Exchange SPE

Ion exchange sorbents separate analytes based on electrostatic interactions between the analyte of interest and the charged groups on the stationary phase. For ion exchange to occur, both the stationary phase and sample must be at a pH where ion-ion interactions may occur.

Anion Exchange

Anion exchange sorbents are derivatized with positively charged functional groups that interact and retain negatively charged anions, such as deprotonated acids. Strong anion exchange sorbents contain quaternary ammonium groups that have a permanent positive charge in aqueous solutions, and weak anion exchange sorbents use amine groups which are charged when the pH is below about 9. Strong anion exchange sorbents are useful because any strongly acidic impurities in the sample will bind to the sorbent and usually will not be eluted with the analyte of interest; to recover a strong acid a weak anion exchange cartridge should be used. To elute the analyte from either the strong or weak sorbent, the stationary phase is washed with a solvent that neutralizes the charge of either the analyte, the stationary phase, or both. Once the charge is neutralized, the electrostatic interaction between the analyte and the stationary phase no longer exists and the analyte will elute from the cartridge.

Cation Exchange

Cation exchange sorbents are derivatized with functional groups that interact and retain positively charged cations, such as protonated amines. Strong cation exchange sorbents contain aliphatic sulfonic acid groups that are always negatively charged in aqueous solution, and weak cation exchange sorbents contain aliphatic carboxylic acids, which are charged when the pH is above about 5. Strong cation exchange sorbents are useful because any strongly basic impurities in the sample will bind to the sorbent and usually will not be eluted with the analyte of interest; to recover a strong base a weak cation exchange cartridge should be used. To elute the analyte from either the strong or weak sorbent, the stationary phase is washed with a solvent that neutralizes ionic interaction between the analyte and the stationary phase.

HPLC

High-performance liquid chromatography (sometimes referred to as high-pressure liquid chromatography), HPLC, is a chromatographic technique used to separate a mixture of compounds in analytical chemistry and biochemistry with the purpose of identifying, quantifying and purifying the individual components of the mixture. Some common examples are the separation and quantitation of performance enhancement drugs (e.g. steroids) in urine samples, or of vitamin D levels in serum. HPLC typically utilizes different types of stationary phases (i.e. sorbents) contained in columns, a pump that moves the mobile phase and sample components through the column, and a detector capable of providing characteristic retention times for the sample components and area counts reflecting the amount of each analyte passing through the detector. The detector may also provide additional information related to the analyte, (e.g., UV/Vis spectroscopic data, if so equipped). Analyte retention time varies depending on the strength of its interactions with the stationary phase, the composition and flow rate of mobile phase used, and on the column dimensions. HPLC is a form of liquid chromatography that utilizes small size columns (typically 250 mm or shorter and 4.6 mm i.d. or smaller; packed with smaller particles), and higher mobile phase pressures compared to ordinary liquid chromatography. With HPLC, a pump (rather than gravity) provides the higher pressure required to move the mobile phase and sample components through the densely packed column. The increased density arises from the use of smaller sorbent particles. Such particles are capable of providing better separation on columns of shorter length when compared to ordinary column chromatography.

The sample to be separated and analyzed is introduced, in a discrete small volume, into the stream of mobile phase percolating through the column. The components of the sample move through the column at different velocities, which are functions of specific physical or chemical interactions with the stationary phase. The velocity of each component depends on its chemical nature, on the nature of the stationary phase (column) and on the composition of the mobile phase. The time at which a specific analyte elutes (emerges from the column) is called the retention time. The retention time measured under particular conditions is considered an identifying characteristic of a given analyte. The use of smaller particle size packing materials require the use of higher operational pressure ("backpressure") and typically improves chromatographic resolution (i.e. the degree of separation between consecutive analytes emerging from the column). Common mobile phases used include any miscible combination of water with various organic solvents (the most common are acetonitrile and methanol). Some HPLC techniques use water free mobile phases (see Normal Phase HPLC below). The aqueous component of the mobile phase may contain buffers, acids (such as formic, phosphoric or trifluoroacetic acid) or salts to assist in the separation of the sample components. The composition of the mobile phase may be kept constant ("isocratic elution mode") or varied ("gradient elution mode") during the chromatographic analysis. Isocratic elution is typically effective in the separation of sample components that are not very dissimilar in their affinity for the stationary phase.

In gradient elution the composition of the mobile phase is varied typically from low to high eluting strength. The eluting strength of the mobile phase is reflected by analyte retention times with high eluting strength producing fast elution (=short retention times). A typical gradient profile in reversed phase chromatography might start at 5% acetonitrile (in water or aqueous buffer) and progress linearly to 95% acetonitrile over 5-25 minutes. Period of constant mobile phase composition may be part of any gradient profile. For example, the mobile phase composition may be kept constant at 5% acetonitrile for 1-3 minutes, followed by a linear change up to 95% acetonitrile.

The composition of the mobile phase depends on the intensity of interactions between analytes and stationary phase (e.g. hydrophobic interactions in reversed-phase HPLC). Depending on their affinity for the stationary and mobile phases analytes partition between the two during the separation process taking place in the column. This partitioning process is similar to that which occurs during a liquid-liquid extraction but is continuous, not step-wise. In this example, using a water/acetonitrile gradient, more hydrophobic components will elute (come off the column) late, once the mobile phase gets more concentrated in acetonitrile (i.e. in a mobile phase of higher eluting strength).

The choice of mobile phase components, additives (such as salts or acids) and gradient conditions depend on the nature of the column and sample components. Often a series of trial runs are performed with the sample in order to find the HPLC method that gives the best separation.

Partition Chromatography

The partition coefficient principle has been applied in paper chromatography, thin layer chromatography, gas phase and liquid-liquid applications. Partition chromatography uses a retained solvent, on the surface or within the grains or fibers of an "inert" solid supporting matrix as with paper chromatography; or takes advantage of some coulombic and/or hydrogen donor interaction with the solid support. Molecules equilibrate (partition) between a liquid stationary phase and the eluent. Known as Hydrophilic Interaction Chromatography (HILIC) in HPLC, this method separates analytes based on polar differences. HILIC most often uses a bonded polar stationary phase and water miscible, high organic concentration, mobile phases. Partition HPLC has been used historically on unbonded silica or alumina supports. Each works effectively for separating analytes by relative polar differences. HILIC bonded phases have the advantage of separating acidic, basic and neutral solutes in a single chromatogram.

The polar analytes diffuse into a stationary water layer associated with the polar stationary phase and are thus retained. Retention strengths increase with increased analyte polarity, and the interaction between the polar analyte and the polar stationary phase (relative to the mobile phase) increases the elution time. The interaction strength depends on the functional groups in the analyte molecule which promote partitioning but can also include coulombic (electrostatic) interaction and hydrogen donor capability.

Use of more polar solvents in the mobile phase will decrease the retention time of the analytes, whereas more hydrophobic solvents tend to increase retention times.

Normal-Phase Chromatography

Normal-phase HPLC (NP-HPLC), or adsorption chromatography, separates analytes based on their affinity for a polar stationary surface such as silica, hence it is based on analyte ability to engage in polar interactions (such as hydrogen-bonding or dipole-dipole type of interactions) with the sorbent surface. NP-HPLC uses a non-polar, non-aqueous mobile phase, and works effectively for separating analytes readily soluble in non-polar solvents. The analyte associates with and is retained by the polar stationary phase. Adsorption strengths increase with increased analyte polarity. The interaction strength depends not only on the functional groups present in the structure of the analyte molecule, but also on steric factors. The effect of steric hindrance on interaction strength allows this method to resolve (separate) structural isomers.

The use of more polar solvents in the mobile phase will decrease the retention time of analytes, whereas more hydrophobic solvents tend to induce slower elution (increased retention times). Very polar solvents such as traces of water in the mobile phase tend to adsorb to the solid surface of the stationary phase forming a stationary hound (water) layer which is considered to play an active role in retention. This behavior is somewhat peculiar to normal phase chromatography because it is governed almost exclusively by an adsorptive mechanism (i.e., analytes interact with a solid surface rather than with the solvated layer of a ligand attached to the sorbent surface, see also reversed-phase HPLC below). Adsorption chromatography is still widely used for structural isomer separations in both column and thin-layer chromatography formats on activated (dried) silica or alumina supports.

Displacement Chromatography

The basic principle of displacement chromatography is: A molecule with a high affinity for the chromatography matrix (the displacer) will compete effectively for binding sites, and thus displace all molecules with lesser affinities. There are distinct differences between displacement and elution chromatography. In elution mode, substances typically emerge from a column in narrow, Gaussian peaks. Wide separation of peaks, e.g., to baseline, is desired in order to achieve maximum purification. The speed at which any component of a mixture travels down the column in elution mode depends on many factors. But for two substances to travel at different speeds, and thereby be resolved, there must be substantial differences in some interaction between the biomolecules and the chromatography matrix. Operating parameters are adjusted to maximize the effect of this difference. In many cases, baseline separation of the peaks can be achieved only with gradient elution and low column loadings. Thus, two drawbacks to elution mode chromatography, especially at the preparative scale, are operational complexity, due to gradient solvent pumping, and low throughput, due to low column loadings. Displacement chromatography has advantages over elution chromatography in that components are resolved into consecutive zones of pure substances rather than "peaks". Because the process takes advantage of the nonlinearity of the isotherms, a larger column feed can be separated on a given column with the purified components recovered at significantly higher concentrations.

Reversed-Phase Chromatography (RPC)

Reversed phase HPLC (RP-HPLC) has a non-polar stationary phase and an aqueous, moderately polar mobile phase. One common stationary phase is a silica which has been surface-modified with $RMe_2SiCl$, where R is a straight chain alkyl group such as $C_{18}H_{37}$ or $C_8H_{17}$. With such stationary phases, retention time is longer for molecules that are less polar, while polar molecules elute more readily (early in the analysis). An investigator can increase retention times by adding more water to the mobile phase; thereby making the affinity of the hydrophobic analyte for the hydrophobic stationary phase stronger relative to the now more hydrophilic mobile phase. Similarly, an investigator can decrease retention time by adding more organic solvent to the eluent. RP-HPLC is so commonly used that it is often incorrectly referred to as "HPLC" without further specification. The pharmaceutical industry regularly employs RP-HPLC to qualify drugs before their release.

RP-HPLC operates on the principle of hydrophobic interactions, which originate from the high symmetry in the dipolar water structure and play the most important role in all processes in life science. RP-HPLC allows the measurement of these interactive forces. The binding of the analyte to the stationary phase is proportional to the contact surface area around the non-polar segment of the analyte molecule upon association with the ligand on the stationary phase. This solvophobic effect is dominated by the force of water for "cavity-reduction" around the analyte and the Cig-chain versus the complex of both. The energy released in this process is proportional to the surface tension of the eluent (water: $7.3 \times 10^{-6}$ J/cm$^2$, methanol: $2.2 \times 10^{-6}$ J/cm$^2$) and to the hydrophobic surface of the analyte and the ligand respectively. The retention can be decreased by adding a less polar solvent (methanol, acetonitrile) into the mobile phase to reduce the surface tension of water. Gradient elution uses this effect by automatically reducing the polarity and the surface tension of the aqueous mobile phase during the course of the analysis.

Structural properties of the analyte molecule play an important role in its retention characteristics. In general, an analyte with a larger hydrophobic surface area (C—H, C—C, and generally non-polar bonds, such as S—S and others) is retained longer because it is non-interacting with the water structure. On the other hand, analytes with higher polar surface area (conferred by the presence of polar groups, such as —OH, —NH$_2$, COO$^-$ or —NH$_3^+$ in their structure) are less retained as they are better integrated into water. Such interactions are subject to steric effects in that very large molecules may have only restricted access to the pores of the stationary phase, where the interactions with surface ligands (alkyl chains) take place. Such surface hindrance typically results in less retention.

Retention time increases with hydrophobic (non-polar) surface area. Branched chain compounds elute more rapidly than their corresponding linear isomers because the overall surface area is decreased. Similarly organic compounds with single C—C-bonds elute later than those with a C=C or C—C-triple bond, as the double or triple bond is shorter than a single C—C-bond.

Aside from mobile phase surface tension (organizational strength in eluent structure), other mobile phase modifiers can affect analyte retention. For example, the addition of inorganic salts causes a moderate linear increase in the surface tension of aqueous solutions (ca. $1.5 \times 10^{-7}$ J/cm$^2$ per Mol for NaCl, $2.5 \times 10^{-7}$ J/cm$^2$ per Mol for (NH$_4$)$_2$SO$_4$), and because the entropy of the analyte-solvent interface is controlled by surface tension, the addition of salts tend to increase the retention time. This technique is used for mild separation and recovery of proteins and protection of their biological activity in protein analysis (hydrophobic interaction chromatography, HIC).

Another important factor is the mobile phase pH since it can change the hydrophobic character of the analyte. For this reason most methods use a buffering agent, such as sodium phosphate, to control the pH. Buffers serve multiple purposes: control of pH, neutralize the charge on the silica surface of the stationary phase and act as ion pairing agents to neutralize analyte charge. Ammonium formate is commonly added in mass spectrometry to improve detection of certain analytes by the formation of analyte-ammonium adducts. A volatile organic acid such as acetic acid, or most commonly formic acid, is often added to the mobile phase if mass spectrometry is used to analyze the column effluent. Trifluoroacetic acid is used infrequently in mass spectrometry applications due to its persistence in the detector and solvent delivery system, but can be effective in improving retention of analytes such as carboxylic acids in applications utilizing other detectors, as it is a fairly strong organic acid. The effects of acids and buffers vary by application but generally improve chromatographic resolution.

Size-Exclusion Chromatography

Size-exclusion chromatography (SEC), also known as gel permeation chromatography or gel filtration chromatography, separates particles on the basis of size. It is generally a low-resolution chromatography and thus it is often reserved for the final, "polishing" step of a purification. It is also useful for determining the tertiary structure and quaternary structure of purified proteins. SEC is used primarily for the analysis of large molecules such as proteins or polymers. SEC works by trapping these smaller molecules in the pores of a particle. The larger molecules simply pass by the pores as they are too large to enter the pores. Larger molecules therefore flow through the column quicker than smaller molecules, that is, the smaller the molecule, the longer the retention time.

This technique is widely used for the molecular weight determination of polysaccharides. SEC is the official technique (suggested by European pharmacopeia) for the molecular weight comparison of different commercially available low-molecular weight heparins.

Ion-Exchange Chromatography

In ion-exchange chromatography (IC), retention is based on the attraction between solute ions and charged sites bound to the stationary phase. Ions of the same charge are excluded. Types of ion exchangers include: polystyrene resins which allow cross linkage which increases the stability of the chain. Higher cross linkage reduces resin swelling, which increases the equilibration time and ultimately improves selectivity; cellulose and dextran ion exchangers (gels) which possess larger pore sizes and low charge densities making them suitable for protein separation: and controlled-pore glass or porous silica. In general, ion exchangers favor the binding of ions of higher charge and smaller radius.

An increase in counter ion (with respect to the functional groups in resins) concentration reduces the retention time. A decrease in pH reduces the retention time in cation exchange while an increase in pH reduces the retention time in anion exchange. By lowering the pH of the solvent in a cation exchange column, for instance, more hydrogen ions are available to compete for positions on the anionic stationary phase, thereby eluting weakly bound cations.

This form of chromatography is widely used in the following applications: water purification, preconcentration of trace components, ligand-exchange chromatography, ion-exchange chromatography of proteins, high-pH anion-exchange chromatography of carbohydrates and oligosaccharides, and others.

Bioaffinity Chromatography

This chromatographic process relies on the property of biologically active substances to form stable, specific, and reversible complexes. The formation of these complexes involves the participation of common molecular forces such as the Van der Waals interaction, electrostatic interaction, dipole-dipole interaction, hydrophobic interaction, and the hydrogen bond. An efficient, biospecific bond is formed by a simultaneous and concerted action of several of these forces in the complementary binding sites.

Aqueous Normal-Phase Chromatography

Aqueous normal-phase chromatography (ANP) is a chromatographic technique which encompasses the mobile phase region between reversed-phase chromatography (RP) and organic normal phase chromatography (ONP). This technique is used to achieve unique selectivity for hydrophilic compounds, showing normal phase elution using reverse-phase solvents.

Isocratic Flow and Gradient Elution

A separation in which the mobile phase composition remains constant throughout the procedure is termed isocratic (meaning constant composition). The mobile phase composition does not have to remain constant. A separation in which the mobile phase composition is changed during the separation process is described as a gradient elution. One example is a gradient starting at 10% methanol and ending at 90% methanol after 20 minutes. The two components of the mobile phase are typically termed "A" and "B"; A is the "weak" solvent which allows the solute to elute only slowly, while B is the "strong" solvent which rapidly elutes the solutes from the column. In reverse-phase chromatography, solvent A is often water or an aqueous buffer, while B is an organic solvent miscible with water, such as acetonitrile, methanol, THF, or isopropanol.

In isocratic elution, peak width increases with retention time linearly according to the equation for N, the number of theoretical plates. This leads to the disadvantage that late-eluting peaks get very flat and broad. Their shape and width may keep them from being recognized as peaks.

Gradient elution decreases the retention of the later-eluting components so that they elute faster, giving narrower (and taller) peaks for most components. This also improves the peak shape for tailed peaks, as the increasing concentration of the organic eluent pushes the tailing part of a peak forward. This also increases the peak height (the peak looks "sharper"), which is important in trace analysis. The gradient program may include sudden "step" increases in the percentage of the organic component, or different slopes at different times—all according to the desire for optimum separation in minimum time.

In isocratic elution, the selectivity does not change if the column dimensions (length and inner diameter) change—that is, the peaks elute in the same order. In gradient elution, the elution order may change as the dimensions or flow rate change.

The driving force in reversed phase chromatography originates in the high order of the water structure. The role of the organic component of the mobile phase is to reduce this high order and thus reduce the retarding strength of the aqueous component.

Parameters

Internal Diameter

The internal diameter (ID) of an HPLC column is one parameter that influences the detection sensitivity and separation selectivity in gradient elution. It also determines the quantity of analyte that can be loaded onto the column. Larger columns are usually seen in industrial applications, such as the purification of a drug product for later use. Low-ID columns have improved sensitivity and lower solvent consumption at the expense of loading capacity. Larger ID columns (over 10 mm) are used to purify usable amounts of material because of their large loading capacity. Analytical scale columns (4.6 mm) have been the most common type of columns. They are used in traditional quantitative analysis of samples and often use a UV-Vis absorbance detector. Narrow-bore columns (1-2 mm) are used for applications when more sensitivity is desired either with special UV-Vis detectors, fluorescence detection or with other detection methods like liquid chromatography-mass spectrometry Capillary columns (under 0.3 mm) are used almost exclusively with alternative detection means such as mass spectrometry. They are usually made from fused silica capillaries, rather than the stainless steel tubing that larger columns employ.

Particle Size

Most traditional HPLC is performed with the stationary phase attached to the outside of small spherical silica particles (very small beads). These particles come in a variety of sizes with 5 μm beads being the most common. Smaller particles generally provide more surface area and better separations, but the pressure required for optimum linear velocity increases by the inverse of the particle diameter squared.

This means that changing to particles that are half as big, keeping the size of the column the same, will double the performance, but increase the required pressure by a factor of four. Larger particles are used in preparative HPLC (column diameters 5 cm up to >30 cm) and for non-HPLC applications such as solid-phase extraction.

Pore Size

Many stationary phases are porous to provide greater surface area. Small pores provide greater surface area while larger pore size has better kinetics, especially for larger analytes. For example, a protein which is only slightly smaller than a pore might enter the pore but does not easily leave once inside.

Pump Pressure

Pumps vary in pressure capacity, but their performance is measured on their ability to yield a consistent and reproducible flow rate. Pressure may reach as high as 40 MPa (6000 lbf/in$^2$), or about 400 atmospheres. Modern HPLC systems have been improved to work at much higher pressures, and therefore are able to use much smaller particle sizes in the columns (<2 μm). These "Ultra High Performance Liquid Chromatography" systems or RSLC/UHPLCs can work at up to 100 MPa (15,000 lbf/in$^2$), or about 1000 atmospheres. The term "UPLC" is a trademark of the Waters Corporation, but is sometimes used to refer to the more general technique.

In chromatography, the simulated moving bed (SMB) technique is a variant of high performance liquid chromatography; it is used to separate particles and/or chemical compounds that would be difficult or impossible to resolve otherwise. This increased separation is brought about by a valve-and-column arrangement that is used to lengthen the stationary phase indefinitely.

In the moving bed technique of preparative chromatography the feed entry and the analyte recovery are simultaneous and continuous, but because of practical difficulties with a continuously moving bed in the simulated moving bed technique instead of moving the bed, the sample inlet and the analyte exit positions are moved continuously, giving the impression of a moving bed.

True moving bed chromatography (MBC) is only a theoretical concept. Its simulation, SMBC is achieved by the use of a multiplicity of columns in series and a complex valve arrangement, which provides for sample and solvent feed, and also analyte and waste takeoff at appropriate locations of any column, whereby it allows switching at regular intervals the sample entry in one direction, the solvent entry; in the opposite direction, whilst changing the analyte and waste takeoff positions appropriately as well.

One advantage of the SMBC is high speed, because a system could be near continuous, whilst, its disadvantage is that it only separates binary mixtures. It does not say, but perhaps it can be assumed that this is equivalent with the separation of a single component from a group of compounds. With regard to efficiency it compares with simple chromatography technique like continuous distillation does with batch distillation.

Specifically, an SMB system has two or more identical columns, which are connected to the mobile phase pump, and each other, by a multi-port valve. The plumbing is configured in such a way that:

a) all columns will be connected in series, regardless of the valve's position;
b) each different position of the valve will reconnect the columns to one another in one possible sequential arrangement of the columns; and
c) all possible positions of the valve will arrange the columns in every possible sequential order.

For example, consider a case where two HPLC columns, A and B, are connected to one another, and the mobile-phase pump, via a six-port, two-position valve (e.g., a Rheodyne 7000). One valve position will distribute the flow in the manner.

Pump→Column A→Column B→Waste, while the other position will distribute the flow in the manner Pump→Column B→Column A→Waste.

Consequently, switching of the valve will "leapfrog" the columns over one another. If elution across two columns in series is not adequate to resolve two compounds in a given run, the eluent can then be made to go through 3, 4, 5 . . . columns in additional runs by carefully timed switching. This increases the number of theoretical plates until separation can be attained.

When affinity differences between molecules are very small, it is sometimes not possible to improve resolution via mobile- or stationary-phase changes. In these cases, the multi-pass approach of SMB can separate mixtures of those compounds by allowing their small retention time differences to accumulate.

At industrial scale an SMB chromatographic separator is operated continuously, requiring less resin and less solvent than batch chromatography. The continuous operation facilitates operation control and integration into production plants.

In size exclusion chromatography, where the separation process is driven by entropy, it is not possible to increase the resolution attained by a column via temperature or solvent gradients. Consequently, these separations often require SMB, to create usable retention time differences between the molecules or particles being resolved. SMB is also very useful in the pharmaceutical industry, where resolution of molecules having different chirality must be done on a very large scale.

Exemplary Methods and Microbes

Once a method is identified that results in a substantially pure preparation of a compound with anti-microbial activity, that method or methods that are similar thereto, e.g., methods that eliminate or add a step and optionally omit testing for activity at each or all separation steps, may be employed to isolate large quantities of the bioactive compound, e.g., isolate about 1 mg to about 1000 mg of a substantially pure preparation per run. Thus, the invention provides a composition, e.g., a powder or liquid composition, having a substantially pure preparation of a compound with anti-microbial activity. That composition may be employed as a neutraceutical or in pharmaceutical compositions.

In one embodiment, the invention provides a method of treating, inhibiting or preventing a bacterial infection, e.g., infection by *Listeria* or a pan resistant gram-negative bacilli, such as *Pseudomonas aeruginosa*, or multi-resistant gram-positive bacteria like methicillin resistant *Staphylococcus aureus*, as well as *Mycobacterium tuberculosis*, or nontuberculosis *Mycobacterium* or *Nocardia*, or *E. coli* in an animal such as a mammal. In one embodiment, the method comprises administering an effective amount of a composition of the invention to a mammal after the mammal has been infected with the bacterium. In one embodiment, the method comprises administering an effective amount of a composition of the invention to the mammal before the mammal is infected with the bacterium.

In one embodiment, the present invention is directed to a method of treating, inhibiting or preventing a viral infection in an animal such as a mammal, e.g., viruses including but not limited to rabies, poxviruses, herpesviruses, influenza A, influenza B, influenza C, flaviviruses including West Nile virus and Dengue virus, paramyxoviruses including Respiratory Syncyctial virus, parvoviruses, retroviruses, poxviruses, hepatitis viruses, and gastroenteroviruses including poliovirus, coxsackie virus, rotavirus, norovirus, and astrovirus. In one embodiment, the method comprises administering an amount of a composition of the invention, e.g., after a mammal has been infected with or exposed to a virus, effective to inhibit or treat the viral infection. In one embodiment, a composition of the invention is administered to a mammal before a mammal is exposed to the virus. In one embodiment, the pathogen is an influenza virus, e.g., influenza A virus. In one embodiment, the influenza A virus is a H5N1 virus strain.

In one embodiment, the invention provides a method of treating, inhibiting or preventing a parasite infection in an animal such as a mammal, e.g., infection by various species of *Plasmodium*, such as *Plasmodium berghei*, and *Plasmodium falciparum* and other *Coccidia* such as *Cryptosporidium parvum*, or other protozoan parasites such as *Trypanosome brucei*, *Entamoeba histolytica*, *Leishmania* species and helminth parasites such as *Schistosoma mansoni*. In one embodiment, the method comprises administering an amount of a composition of the invention to the mammal effective to inhibit or treat the parasitic infection after the mammal has been infected with the parasite. In one embodiment, a composition of the invention is administered to a mammal before the mammal is exposed to the parasite.

In one embodiment, the invention provides a method of treating, inhibiting or preventing a fungal infection in an animal, e.g., *Cryptococcus*, *Aspergillus*, species, *Histoplasma capsulatum*, *Blastomyces dermatitidis*, *Coccidiomycosis immitis* and *Penicillium marcenscens*. In one embodiment, the method comprises administering an effective amount of a composition of the invention to the mammal after the mammal has been infected with the fungus. In one embodiment, the method comprises administering an effective amount of a composition of the invention to the mammal before the mammal is infected with the fungus.

As will be apparent to one skilled in the art, the optimal concentration of the active agent in a composition of the invention will necessarily depend upon the specific agent(s) used, the characteristics of the animal, e.g., avian or mammal, and the nature of the microbial infection. These factors can be determined by those of skill in the medical and pharmaceutical arts in view of the present disclosure. In general, the active agent(s) in the composition of the invention are administered at a concentration that either modulates anti-microbial activity against microbial infection or modulates an immune response allowing the host to recover from or clear a microbial infection, without significant, harmful or adverse side effects.

Specific dosages may be adjusted depending on conditions of disease, the age, body weight, ethnic background, general health conditions, sex, diet, lifestyle and/or current, therapeutic regimen of the animal, as well as for intended dose intervals, administration routes, excretion rate, and combinations of drugs. Any of the dosage forms described herein containing effective amounts are well within the bounds of routine experimentation and therefore, well within the scope of the instant disclosure.

A composition may comprise a compound of the invention in an amount of about 1 µg to about 2000 mg of the compound per dose for a mammal weighing about 20 to 25 g. In one embodiment, the composition comprises a compound of the invention an amount of about 1 mg to about 1000 mg, e.g., about 10 mg to about 100 mg, or an amount of about 0.1 µg to about 1000 µg, e.g., about 1 µg to about 10 µg. In one embodiment, the composition comprises a compound of the invention an amount of about 20 µg/kg to about 2000 µg/kg, e.g., about 50 µg/kg to about 500 µg/kg or about 100 µg/kg to about 400 µg/kg.

The desired dose of the composition may be presented in a continuous infusion, a single dose, or as divided doses administered at appropriate intervals, for example as two, three, four or more sub-doses per day. Optionally, a dose of composition may be administered on one day, followed by one or more doses spaced as desired thereinafter. In one exemplary embodiment, an initial dose is given, followed by a dose of the same composition approximately two to four days later. In one particular embodiment, the mammal is administered a first dose of the composition at about 48 hours post-infection and a second dose of the composition at about 96 hours post-infection. Other dosage schedules may also be used.

Following an initial administration of the composition, animals may receive one or several doses adequately spaced thereafter. In some embodiments, the subsequent doses comprise the same amounts and type of active agent as the initial administration. In other embodiments, the subsequent doses may comprise a reduced amount and/or a different type of active agent.

In addition to the active agent(s), one or more suitable pharmaceutically acceptable earners may be used. As used herein, the term "pharmaceutically acceptable carrier" refers to an acceptable vehicle for administering a composition to mammals comprising one or more non-toxic excipients that do not react with or reduce the effectiveness of the pharmacologically active agents contained therein. The proportion and type of pharmaceutically acceptable carrier in the composition may vary, depending on the chosen route of administration. Suitable pharmaceutically acceptable carriers for the compositions of the present disclosure are described in the standard pharmaceutical texts. See, e.g., "Remington's Pharmaceutical Sciences", 18$^{th}$ Ed., Mack Publishing Company, Easton, Pa. (1990). Specific non-limiting examples of suitable pharmaceutically acceptable carriers include water, saline, dextrose, glycerol, ethanol, or the like and combinations thereof.

Optionally, the composition may further comprise minor amounts of auxiliary substances such as agents that enhance the antimicrobial effectiveness of the preparation, stabilizers, preservatives, and the like.

In one embodiment, the composition may also comprise a bile acid or a derivative thereof, in particular in the form of a salt. These include derivatives of cholic acid and salts thereof, in particular sodium salts of cholic acid or cholic acid derivatives. Examples of bile acids and derivatives thereof include cholic acid, deoxycholic acid, chenodeoxycholic acid, lithocholic acid, ursodeoxycholic acid, hyodeoxycholic acid and derivatives such as glyco-, tauro-, amidopropyl-1-propanesulfonic-, amidopropyl-2-hydroxy-1-propanesulfonic derivatives of the aforementioned bile acids, or N,N-bis(3-D-gluconoamidopropyl)deoxycholamide. A particular example is sodium deoxycholate (Na-DOC).

Examples of suitable stabilizers include sugars such as sucrose and glycerol, encapsulating polymers, chelating agents such as ethylenediaminetetracetic acid (EDTA), proteins and polypeptides such as gelatin and polyglycine and combinations thereof.

Depending on the route of administration, the compositions may take the form of a solution, suspension, emulsion, or the like. A composition of the invention can be administered intranasally or through enteral administration, such as orally, or through subcutaneous injection, intra-muscular injection, intravenous injection, intraperitoneal injection, or intra-dermal injection to a mammal, e.g., humans, horses, other mammals, etc. Compositions may be formulated for a particular route of delivery, e.g., formulated for oral delivery.

For parenteral administration, the composition of the invention may be administered by intravenous, subcutaneous, intramuscular, intraperitoneal, or intradermal injection, and may further comprise pharmaceutically accepted earners. For administration by injection, the composition may be in a solution in a sterile aqueous vehicle which may also contain other solutes such as buffers or preservatives as well as sufficient quantities of pharmaceutically acceptable salts or of glucose to make the solution isotonic.

The composition may be delivered to the respiratory system, for example to the nose, sinus cavities, sinus membranes or lungs, in any suitable manner, such as by inhalation via the mouth or intranasally. The composition may be dispensed as a powdered or liquid nasal spray, suspension, nose drops, a gel or ointment, through a tube or catheter, by syringe, by packtail, by pledget, or by submucosal infusion. The composition may be conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the composition and a suitable powder base such as lactose or starch. Examples of intranasal formulations and methods of administration can be found in PCT publications WO 01/41782, WO 00/33813, and U.S. Pat. Nos. 6,180,603; 6,313,093; and 5,624,898, all of which are incorporated herein by reference and for all purposes. A propellant for an aerosol formulation may include compressed air, nitrogen, carbon dioxide, or a hydrocarbon based low boiling solvent. The composition of the invention may be conveniently delivered in the form of an aerosol spray presentation from a nebulizer or the like. In some aspects, the active ingredients are suitably micronized so as to permit inhalation of substantially all of the active ingredients into the lungs upon administration of the dry powder formulation, thus the active ingredients will have a particle size of less than 100 microns, desirably less than 20 microns, and preferably in the range 1 to 10 microns. In one embodiment, the composition is packaged into a device that can deliver a predetermined, and generally effective, amount of the composition via inhalation, for example a nasal spray or inhaler.

Pharmaceutical Formulations

The compositions of this invention may be formulated with conventional carriers and excipients, which will be selected in accord with ordinary practice. Aqueous formulations are prepared in sterile form, and when intended for delivery by other than oral administration, will generally be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone they may be present as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

Pharmaceutical formulations according to the present invention may include one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft, capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or w-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for intrapulmonary or nasal administration may have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of a given condition.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Exemplary unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials that are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

An effective dose of an active ingredient depends at least on the nature of the condition being treated, toxicity, whether the active ingredient is being used prophylactic-ally (e.g., lower doses may be employed), the method of delivery, and the pharmaceutical formulation, and will be determined by the clinician using conventional dose escalation studies, it can be expected to be from about 0.0001 to about 100 mg/kg body weight per day. Typically, from about 0.01 to about 10 mg/kg body weight per day, including from about 0.01 to about 5 mg/kg body weight per day, or from about 0.05 to about 0.5 mg/kg body weight, per day. For example, the daily candidate dose for an adult human of approximately 70 kg body-weight will range from 1 mg to 1000 mg, e.g., from 5 mg to 500 mg, and may take the form of single or multiple doses. For instance, about 5 mg to about 750 mg, e.g., about 10 mg to about 70 mg, or any integer in between, of the active ingredient may be administered to a human.

The invention will be further described by the following non-limiting examples.

Example I

Example I—Separation of Compounds From 90MX Cranberry Powder

Figure 1:
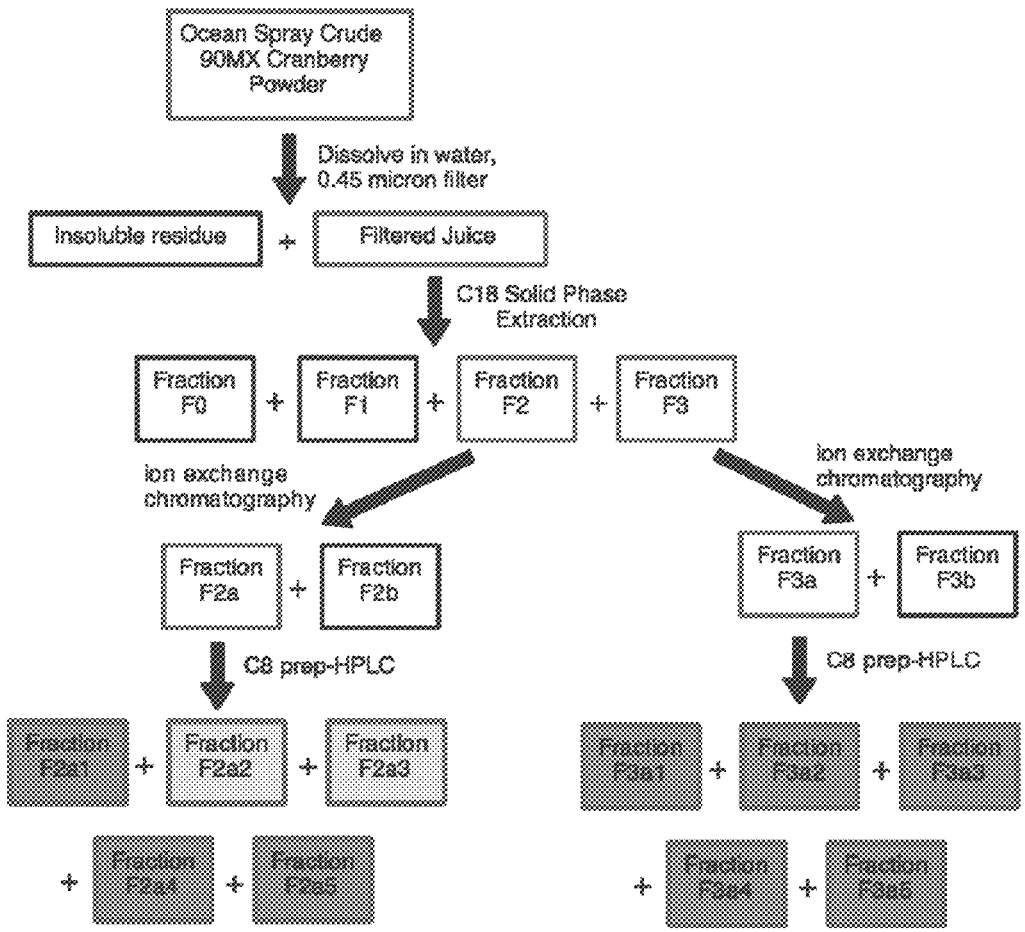
FIG. 1. Schematic of an exemplary separation protocol using cranberry juice fractions. Boxes represent cranberry juice fractions. Red borders indicate fractions with strong activity against vaccinia virus. Black borders indicate fractions with weak or no antiviral activity. Boxes shaded with yellow indicate fractions that have good water solubility and purity. Fractions shaded pink include those with low water solubility or low purity levels. Arrows represent, separation methods applied to purify a fraction further.
Figure 2:
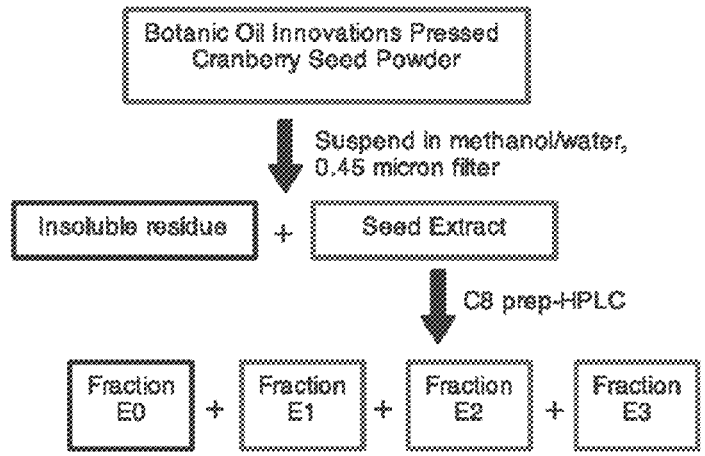
FIG. 2. Schematic of an exemplary separation protocol with cranberry seed fractions. Boxes represent cranberry seed fractions. Red borders indicate fractions with strong activity against vaccinia virus. Black borders indicate fractions with weak or no antiviral activity. Arrows represent separation methods applied to purify a fraction further.
Figure 3:
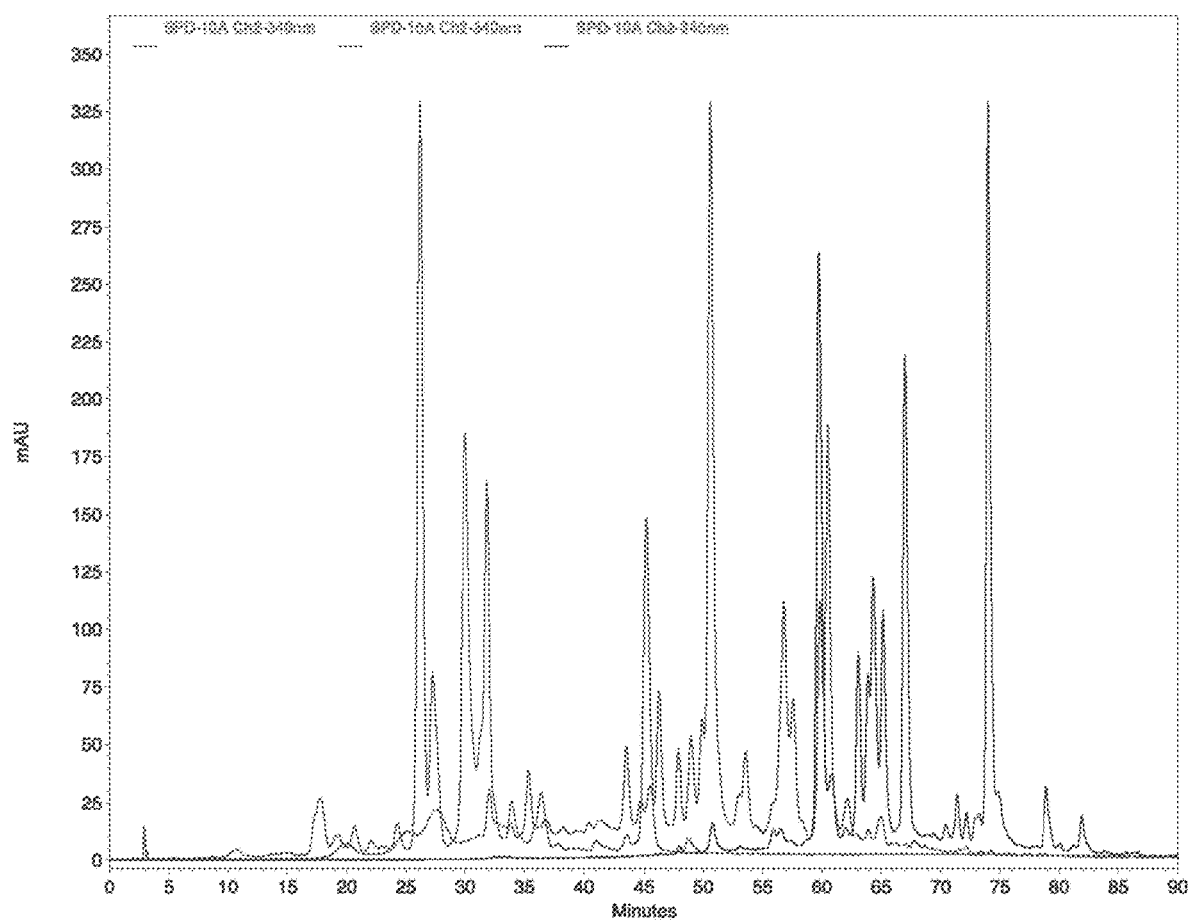

Stage 1 Separation: C18 Solid Phase Extraction. Ocean Spray cranberry powder, 90MX was reconstituted in water to cranberry juice and filtered through a 0.45 µm membrane. The filtered juice was loaded on a CIS solid phase extraction column (Extract-Clean brand, standard CIS, 50 µm particle size, 60 angstrom pore size, Grace Davidson Discovery Sciences). The column was then washed with water (to yield fraction F0) followed by elution with 15% methanol (F1), 25% methanol (F2), and 100% methanol (F3). Fraction F0 was evaporated yielding a white powder that, was about 94% of the total mass and was inactive in the vaccinia anti-viral assay. Fractions F1, F2, and F3 were evaporated yielding red powders, which accounted for about 6% of the total mass of the 90MX powder. FIG. 3 shows analytical HPLC chromatograms for fractions F1, F2, and F3 detected by UV at 340 nm. Fractions F2 and F3 had strong antiviral activity.

Figure 4:
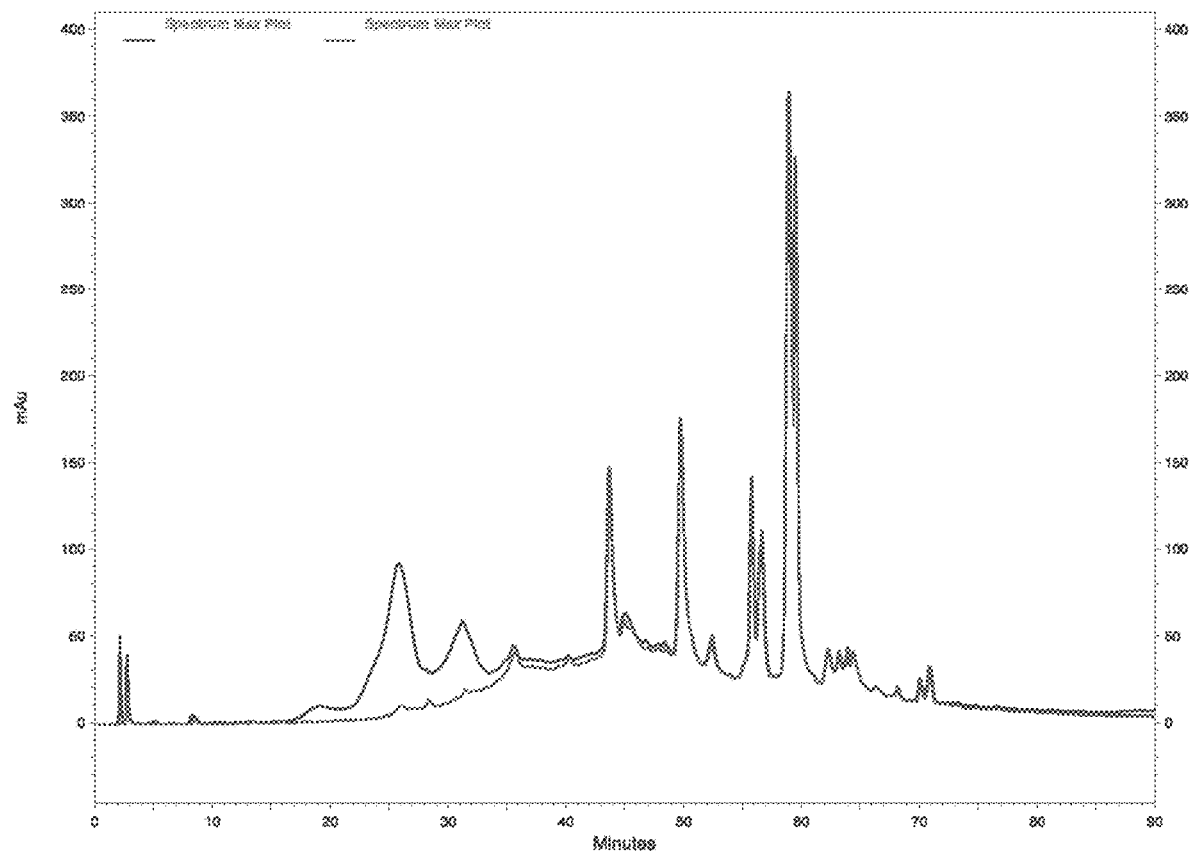

Stage 2 Separation: Strong Cation Exchange Chromatography. Fractions F2 and F3 were each dissolved in a solution of methanol and water and loaded onto a strong cation exchange column (Redi-Sep Rf SCX brand, silica based, 40-63 µm particle size, 100 angstrom pore size, Isco-Teledyne) and eluted with a mixture of methanol and water. Cationic anthocyanin components were retained, and the eluent gave fractions F2a and F3a, respectively. Elution was monitored by UV and proceeded until the signal at 340 nm had decreased to zero. These fractions had strong antiviral activity. FIG. 4 compares analytical HPLC chromatograms for fractions F2 and F2a (before and after stage 2 separation), using diode array UV detection from 250-600 nm. Anthocyanin fractions could be eluted from the columns using a solution of water, methanol, hydrochloric acid and sodium chloride, giving fractions F2b and F3b, respectively. These fractions contained red anthocyanin pigments and lacked antiviral activity.

Figure 5:
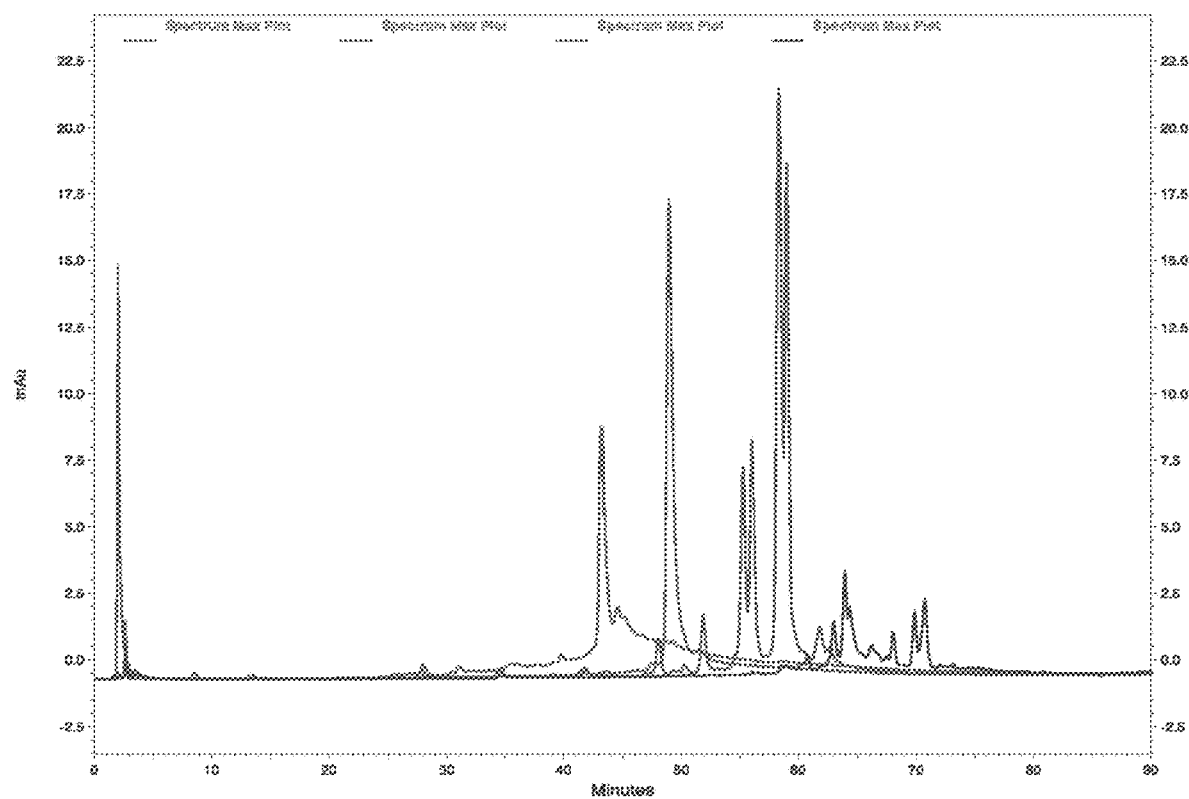

Stage 3 Separation: Preparative Scale High Performance Liquid Chromatography. To further separate components in fraction F2a, prep HPLC was employed. The column used was a Waters Symmetry brand, C8 phase, with 7 µm particle size, and dimensions of 19×150 mm, operated at a flow rate of 12 mL/min. A binary solvent gradient was used for this HPLC separation with solvent A=water+0.1% formic acid and solvent B=methanol+0.1% formic acid. Solvent composition at various times was as follows, time (percent B): initial (10% B), 50 min. (35% B), 80 min. (60% B), 85 min. (80% B), 90 min. (80% B). Individual runs contained about 40 mg of dry F2a fraction dissolved in 1:1 water/methanol to a volume of 1 mL. The progress of the separation was followed using UV detection at 255 and 340 nm. Eluent was collected in tubes at 2 minute intervals and the contents of these tubes was pooled according to their UV profile to yield fractions F2a1, F2a2, F2a3, F2a4, and F2a5. Evaporation of the solvent from each of these fractions yielded dry powders. FIG. 5 shows overlaid analytical HPLC chromatograms for fractions F2a2, F2a3, F2a4, and F2a5 detected by diode array UV from 250-600 nm.

Figure 6A:
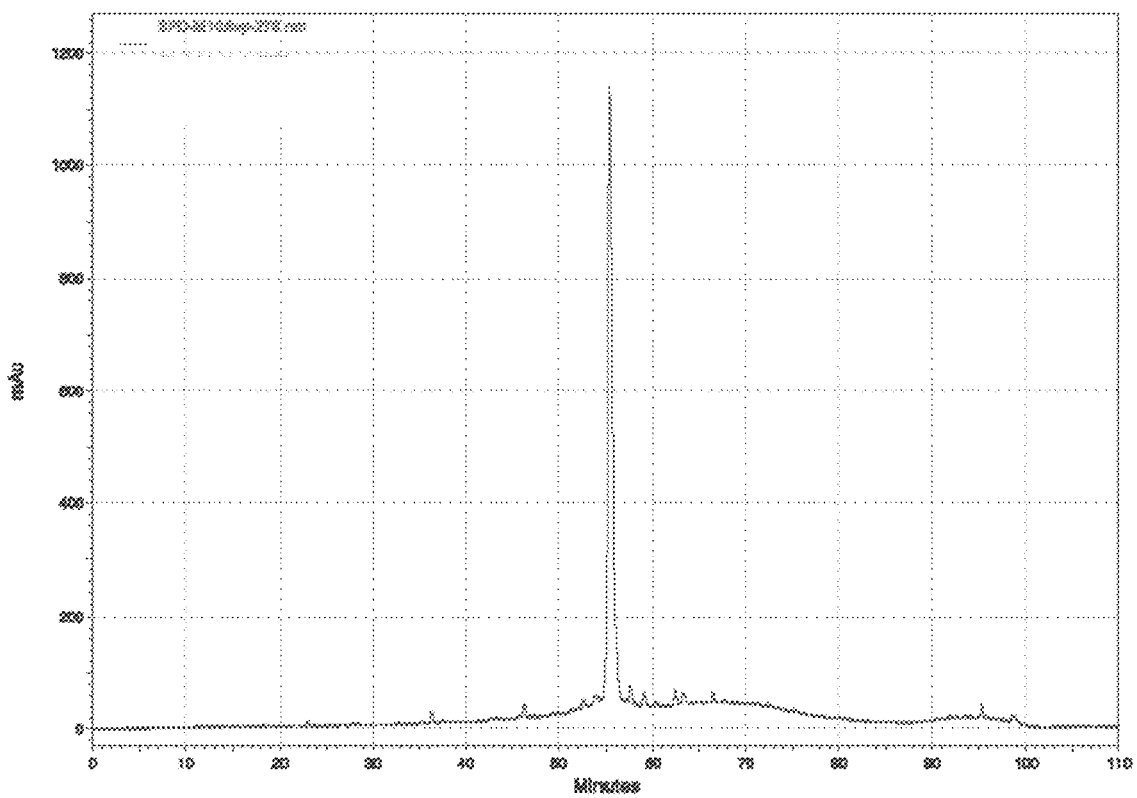
FIGS. 6A and 6B. These show analytical HPLC chromatographs that were used to carry out final purification of fractions F2a2 and F2a3 by collecting the peaks eluting at 56 min. and 50 min., respectively. Fraction F2a2 was purified using a Luna brand pentafluorophenyl (2) phase column from Phenomenex of dimensions 4.6×150 mm, with a 5 µm particle size and a flow rate 0.5 mL/min. The same gradient solvent program was used as before for the C8 column. Peaks in FIGS. 6A and 6B were acquired at 277 nm and 356 nm, respectively.
Figure 6B:
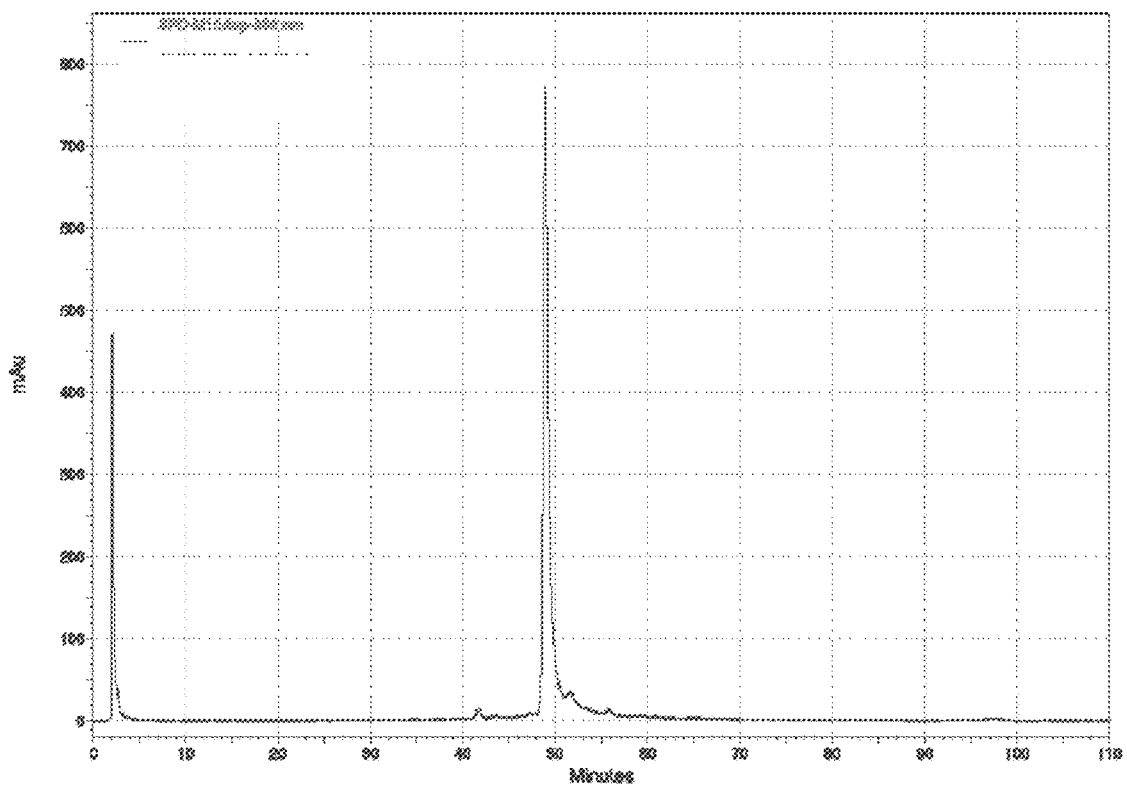

Stage 4 Separation: Analytical Scale High Performance Liquid Chromatography. As a final purification step, fractions F2a2 and F2a3 were separated by analytical HPLC. For F2a2, the following column was used: Phenomenex Luna brand pentafluorophenyl 2 phase (PFP 2) of dimensions 4.6×150 mm, 5 µm particle size, and operated at a flow rate of 0.5 mL/min. For F2a3, the following column was used: Waters Symmetry brand C8 phase of dimensions 3.9×150 mm, 5 µm particle size, operated at a flow rate of 0.5 mL/min. In both cases the same binary solvent gradient was used for HPLC separation with solvent A=water+0.1% formic acid and solvent B=methanol+0.1% formic acid. Solvent composition at various times was as follows, time (percent B): initial (10% B), 50 min. (35% B), 80 min. (60% B), 85 min. (80% B), 90 min. (80% B), FIGS. 6A and 6B show analytical HPLC chromatograms for fractions F2a2 detected by UV at 277 nm and F2a3 detected by UV at 356 nut, respectively.

Figure 7:
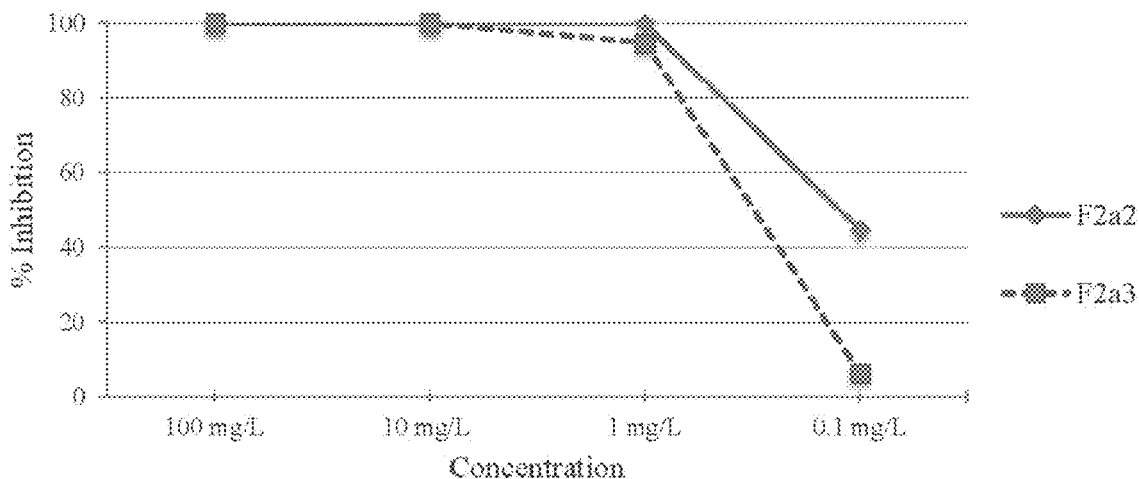
FIG. 7. Anti-viral activity against vaccinia virus of powder fractions F2a2 and F2a3 after separation and removal of solvent.

Antiviral Results for F2a2 and F2a3 Against Vaccinia Virus:

FIG. 7 shows the anti-vaccinia virus activities of compounds F2a2 and F2a3 at solution concentrations ranging from 100 mg/L to 0.1 mg/L. Activity is reported as a percentage vaccinia infection inhibition in treated cells compared to untreated controls. Both materials completely inhibited vaccinia at concentrations of 10 mg/L and higher. At the more dilute concentration of 1 mg/L, both compounds retained greater than 90% inhibition potency. At the even more dilute concentration of 0.1 mg/L activity dropped off to 45% and 6% for F2a2 and F2a3, respectively.

Figure 8:
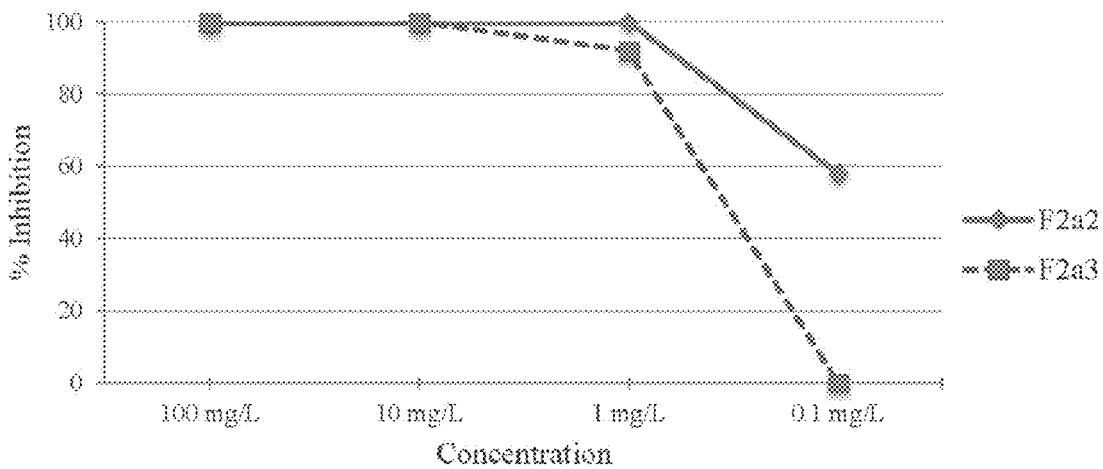
FIG. 8. Anti-viral activity against poliovirus 1 of powder fractions F2a2 and F2a3 after separation and removal of solvent.
Figure 9:
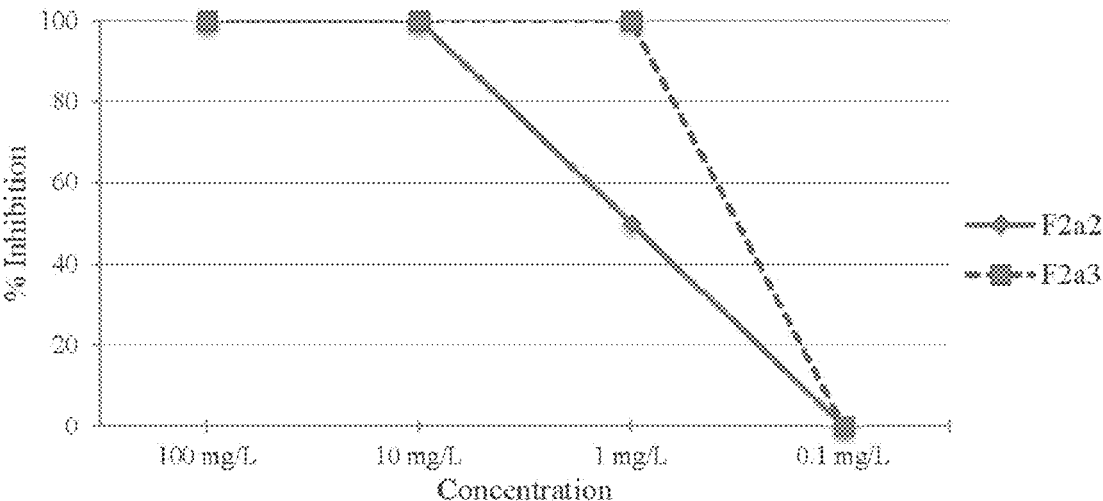
FIG. 9. Anti-viral activity against influenza A/H1N1 of powder tractions F2a2 and F2a3 after separation and removal of solvent.
Figure 10:
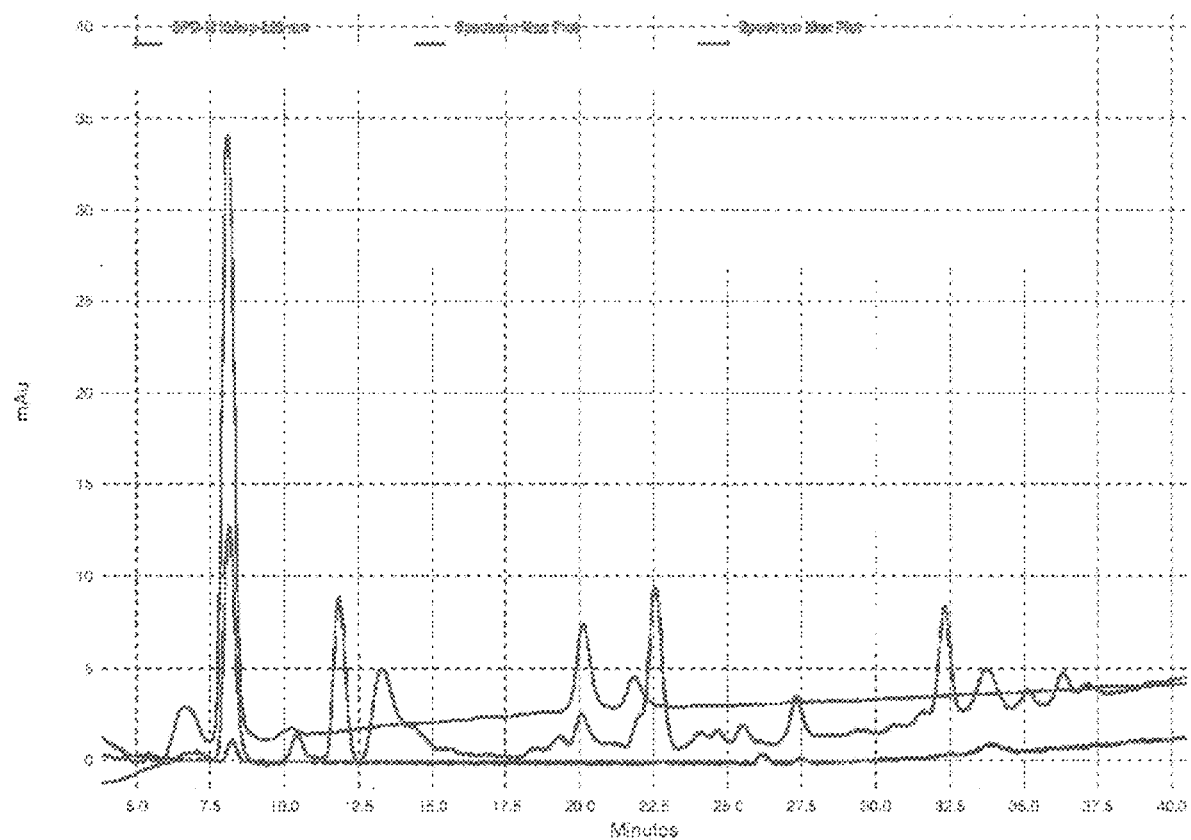
FIG. 10. Overlaid HPLC chromatograms are shown of fractions E1, E2, and E3 separated by prep-scale C8 HPLC. A Waters Symmetry C8 column was used for prep HPLC, 19×150 mm, 7 µm, with a flow rate of 12 mL/min. The same solvent program as was used in C8 analytical HPLC was used for prep HPLC. All traces in FIG. 10 were recorded over a range of wavelengths from 250 to 600 nm.
Figure 11:
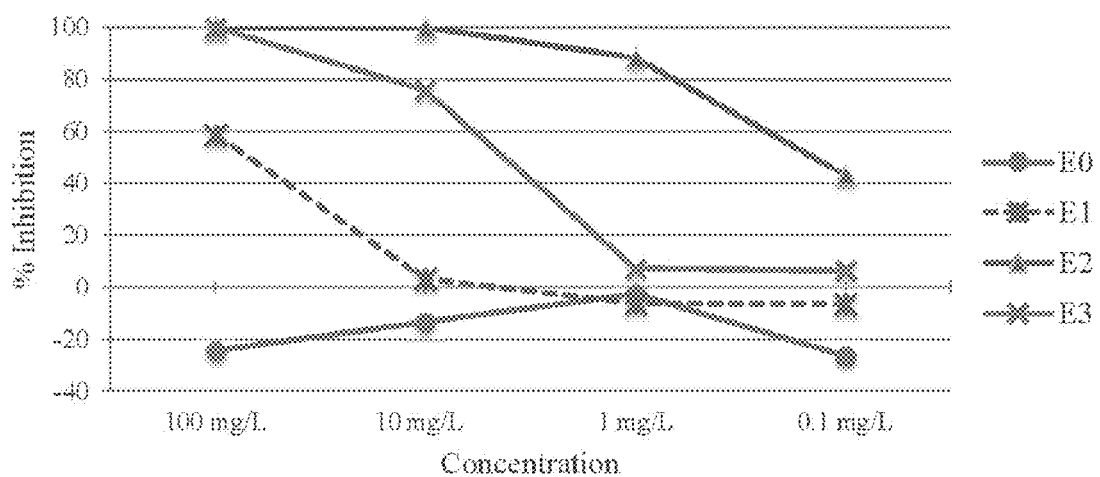
FIG. 11 shows the anti-viral activity against vaccinia virus of powder fractions of E0, E1, E2, and E3 after separation and removal of solvent.
Figure 12:
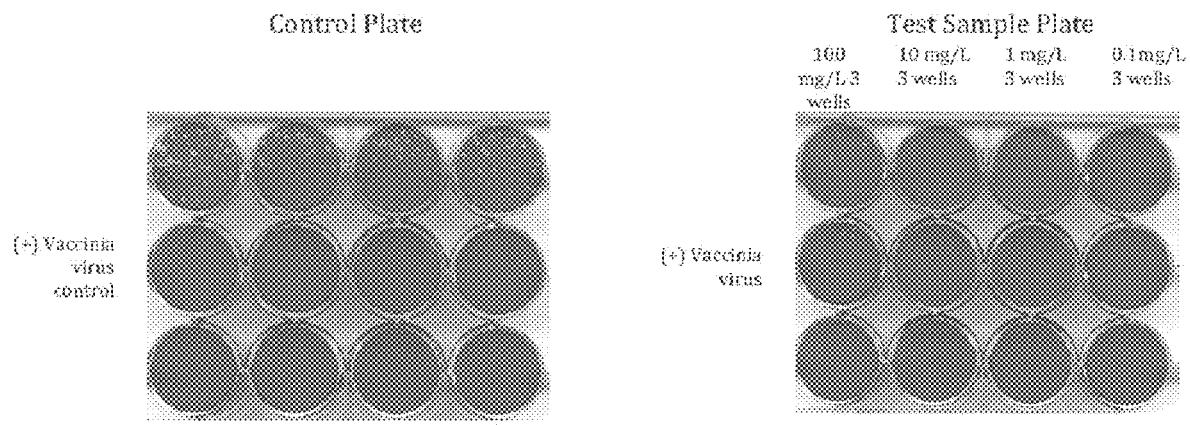
FIGS. 12-14 show examples of antiviral testing data in tests. To prepare samples for testing, they were diluted in MEM/EB88 cell culture medium (HyClone catalog #SH30024.01) to test at concentrations of 100 mg/L, 10 mg/L, 1 mg/L and 0.1 mg/L. Samples that were not soluble in the MEM/EBSS were first diluted to 10 mg/L in DMSO (Fisher BioReagents catalog #BP231-100). A control experiment was performed to demonstrate that the DMSO did not affect viral activity or cell growth.
Figure 13:
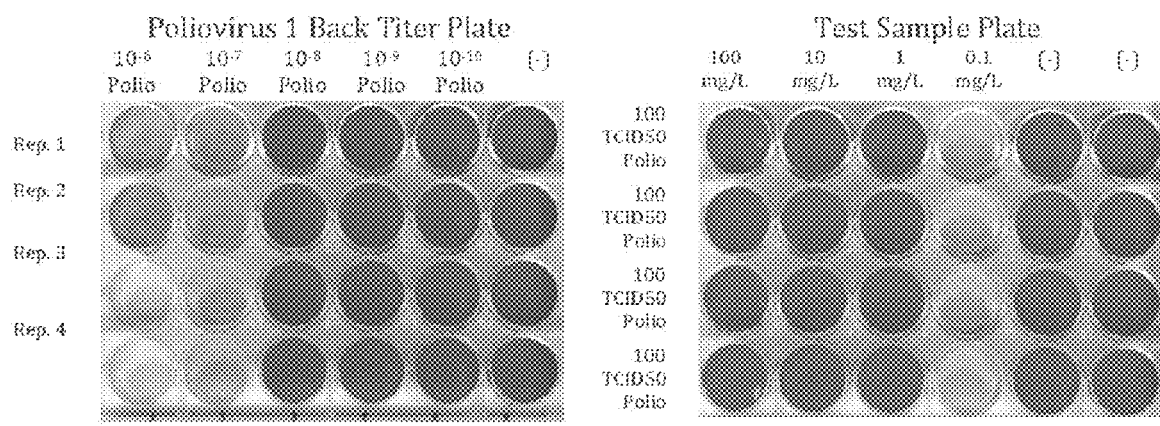

Antiviral Results for F2a2 and F2a3 Against 100 TCID50 Poliovirus 1:

FIG. 8 shows the anti-poliovirus 1 activities of compounds F2a2 and F2a3 at solution concentrations ranging from 100 mg/L to 0.1 mg/L. Activity is reported as a percentage poliovirus 1 infection inhibition in treated ceils compared to untreated controls. Both materials completely inhibited vaccinia at concentrations of 10 mg/L and higher. At the more dilute concentration of 1 mg/L, both compounds retained greater than 90% inhibition potency. At the even more dilute concentration of 0.1 mg/L activity dropped off to 45% and 6% for F2a2 and F2a3, respectively.

Antiviral Results for F2a2 and F2a3 Against 10 TCID50 Influenza A/H1N1:

FIG. 9 shows the anti-influenza A/H1N1 activities of compounds F2a2 and F2a3 at solution concentrations ranging from 100 mg/L to 0.1 mg/L. Activity is reported as a percentage influenza A/H1N1 infection inhibition in treated cells compared to untreated controls. Both materials completely inhibited vaccinia at concentrations of 10 mg/L and higher. At the more dilute concentration of 1 mg/L, F2a3 maintained 100% inhibition while the activity of F2a2 fell to 50%. Both compounds were inactive against influenza A/H1N1 at the more dilute concentration of 0.1 mg/L.

Example II—Compounds from Cranberry Seed Powder

Separation of Cranberry Seed Powder

FIG. 2 shows a separation protocol that was employed with a cranberry seed powder. Botanic Oil Innovations Cranberry Seed Nutri-Powder was extracted according to the following protocol. The powder (5 g) was mixed with 70% methanol/30% water solution (100 mL) for 30 minutes. Then Celite (1 g) was stirred in and the mixture was vacuum filtered through a pad of Celite. Solvents were removed under vacuum to give a red-brown powder (0.74 g). This material was separated using preparative HPLC using the following column: Waters Symmetry brand, C8 phase, with 7 μm particle size, and dimensions of 19×150 mm, operated at a flow rate of 12 mL/min. A binary solvent gradient was used for this HPLC separation with solvent A=water+0.1% formic acid and solvent B=methanol+0.1% formic acid. Solvent composition at various times was as follows, time (percent B): initial (10% B), 50 min. (35% B), 80 min. (60% B), 85 min. (80% B), 90 min. (80% B). Individual runs contained about 40 mg of dry seed extract dissolved as a solution of water/methanol to a volume of 1 mL. The progress of the separation was followed using UV detector at 255 and 340 nm. Eluent was collected in tubes at 2 minute intervals and the contents of these tubes was pooled according to their UV profile to yield fractions labeled as E0-E3. Analytical HPLC chromatograms of fractions E1, E2, and E3 are overlaid in FIG. 10.

Antiviral Activity of Fractions E0, E1, E2 and E3 Against Vaccinia Virus:

FIG. 11 shows the anti-vaccinia virus activities of fractions E0, E1, E2 and E3 at solution concentrations ranging from 100 mg/L to 0.1 mg/L. Activity is reported as a percentage vaccinia infection inhibition in treated cells compared to untreated controls. Fraction E2 was the most active, followed by E3 and then E1. Fraction E0 was inactive at ail concentrations. Fractions E2 and E3 both inhibited vaccinia at 100% at a concentration of 100 mg/mL, while E1 inhibited vaccinia at 59% at this concentration. At the more dilute concentration of 10 mg/L, fractions E2 and E3 exhibited 100% and 76% vaccinia inhibition, respectively, while E1 was essentially inactive at this concentration. Upon further dilution to a concentration of 1 mg/L, E2 maintained 88% vaccinia inhibition while E3 was essentially inactive at this concentration. At a concentration of 0.1 mg/L the anti-vaccinia activity of E2 was 43% inhibition.

TABLE 1

Anti-viral Drug Candidate Compounds

| Name | Starting Material of Compound | Characteristics |
| --- | --- | --- |
| F2a3 | Ocean Spray Crude 90MX Powder | See FIG. 1. Identified to be myricetin β-3 galactoside using proton nuclear magnetic resonance spectroscopy ($^1$H NMR), MALDI-TOF mass spectrometry. Water soluble, stable, flavonol. Absorbs at 340 nm. It has anti-viral activity against vaccinia virus. One structural analog, quercetin-β-3-galactoside (which has the same sugar pendent group, but a different core) was found to be inactive. |
| F2a2* | Ocean Spray Crude 90MX Powder | See FIG. 1. Isolated and purified. It is water soluble. It is not a flavonol and absorbs at 277 nm. It is stable and has strong anti-viral activity against vaccinia virus. |
| E2 | Botanic Oil Innovations Pressed Cranberry Seed Powder | This material is very easy to purify because it is extremely stable, polar and water-soluble (FIG. 2). It quickly flows through the first extraction C18 column. It has strong anti-viral activity against vaccinia virus. |

*Preliminary data suggests it may be the strongest inhibitor of the three.

All of the compounds described in Table 1 are water-soluble making them easy to purify. They are all very stable compounds, e.g., stable during a drying procedure, e.g., rotavapping at 40° C. (body temperature is 37° C.) and stable at room temperature in powder form. These small molecule compounds are not susceptible to protease activity. No added chemicals are required to solubilize them for mass production or therapeutic applications. The compounds became more potent at each purification step.

Example III

SMBC technology allows complex mixtures such as cranberry juice to be simplified into two fractions with each separation run, which are defined as “raffinate” and “extract” fractions, and may increase productivity up to 20 fold and reduce costs, e.g., up to 90%, relative to other methods. There are a number of parameters that are optimized for each mixture separated in the process including mobile phase composition, flow rates and valve switching times. When adjusted, the raffinate and extract fractions each contain roughly half of the compounds in the original mixture. These fractions are then tested for anti-microbial activity, e.g., in plaque reduction assays against vaccinia virus. Fractions that display activity are then separated via a second round of SMBC chromatography with a new chromatographic method with modified parameters, which will produce two new fractions. Each of these fractions are in turn tested for activity, and the process repeated in an iterative fashion until pure active compounds have been isolated. Using this strategy a very complex mixture can be separated in a minimal number of chromatographic cycles. It is estimated each pure active compound may be produced in as few as eight cycles. Each chromatographic cycle, including development time, separation run time, solvent removal, and associated biological testing, may be completed in about 1 to 2 weeks. Once lead compounds have been thoroughly purified through chromatography, their chemical structures are determined by proton and carbon NMR spectroscopy, infrared spectroscopy, mass spectrometry, and elemental analyses.

C8 Column Runs to Separate Fraction F2a

F2 was dissolved in 50% $H_2O$/MeOH+0.1% formic acid at 10 μg/mL and 0.5 mL was injected onto a C8 column at a flowrate of 5 mL/min. Isocratic runs were done at 40%, 45%, 50% and 55% MeOH and output was monitored at 255 nm (red) and 520 nm (blue). The peaks in the blue trace were from anthocyanins. The 50% and 55% MeOH runs looked the same and 50% MeOH was used for subsequent runs.

The Octave 100 was set to run in SMBC mode, with each of the systems 8 C8 88.2 mL volume columns connected to the valve block and flushed with the mobile phase. Pump 1 was designated as the feed pump. Pump 2 was the desorbant pump, moving the elution solvent 50/50 $H_2O$/MeOH with 0.1% formic acid. Pump 3 was not used, and pump 4 was attached to outlet "E" to meter the extract flow rate. A script was developed using an online calculator to optimize flow rates in the different zones. The following parameters were entered into the 3-zone calculator.

Column Measurements
Column Volume ml, 19.6 "a"
Flow Rate for $t_0$, ml/min, 5.00 "b"
$t_0$ min., 1.60 "a"
Void Fraction of Adsorbent, 0.40 "a"
Fast Peak 1 $t_R$ min, 3.10 "b"
Slow Peak 2 $t_R$ min, 5.60 "b"
Henry Constants
H1 is 0.65
H2 is 1.72
Selectivity is 2.66
SMBC System Measurements
Column Volume ml, 88.2 "a"
Extra Column Volume ml, 3.90 "a"
Switch Time seconds, 600 "c"
$Q_{feed}$ ml/min, 5 "c"
$Q_{desorbent}$ ml/min, 18 C
$Q_{extract}$ ml/min, 10
$Q_{raffinate}$ ml/min, 13.00
$Q_1$ ml/min, 18.00
$Q_2$ ml/min, 8.00
$Q_3$ ml/min, 13.00
$m_1$, 2.68
$m_2$, 0.76
$m_3$, 1.72
Mass Balance ml/min, 23.00
m1>H2>m3>m2>H1
a=constants
b=conditions determined, first, experiment
c=conditions varied in the calculator. $Q_{feed}$ and $Q_{desorb}$ are solvent inputs, $Q_{extract}$ and $Q_{raffinate}$ are solvent outputs, and $Q_{feed}+Q_{desorb}=Q_{extract}+Q_{raffinate}$
$Q_{feed}$ usually about ¼ to ⅕ of $Q_{desorb}$
If $Q_{desorb}$ is decreased, switch time usually needs to be increased
Some combinations don't work in practice due to back pressure limitations.

These include
   The pressure at any point can't exceed 295 psi. Pressure is usually greatest within the loop of columns at the desorbant pump,
   The pressure at the end of the extract line must exceed the pressure at the desorbant pump by about 40 psi or more, or the flowrates out of raffinate and extract lines may not be correct. This can be achieved by placing a back pressure regulator after the extract, to increase pressure at pump 4 (extract) vs. pump 2 (desorbant).
   The configuration that was used placed a 250 psi BPR on the extract output and a 40 psi BPR on the raffinate output. The raffinate BPR may have been optimal, but helped maintain at least some pressure on the feed pump, which otherwise operated near 0 psi. They also helped keep gas bubbles out of the detector flow cells that were hooked to raffinate and extract lines.
   The raffinate stream was monitored by UV at 520 nm and the extract stream monitored at 255 nm. The script used was a standard 3-2-3 isocratic SMBC script with specific flow rates for this system substituted in. After step 1 in an eight step script, subsequent steps move all inlets and outlets one column position to the right. The feed solution for this separation was F2 dissolved in 50/50 $H_2O$/MeOH+0.1% formic acid at 10 mg/μL.

Pressures while operating this script.
Pump 2=205 psi
Pump 1=23 psi
Pump 4=247 psi
Column switching occurred every 600 sec. At column switches the extract, signal was maximal and decreased over time as that batch moves past the extract outlet. The raffinate came out bright red while the extract was pale yellow. Solvent was removed from each solution by rotovapping and then lyophilization. This worked well for the raffinate, which gave a red solid. HPLC results at 340 nm and 521 ran, as well as spectral plots, showed two strongly absorbing bands between 22-34 minutes at 521 nm indicating anthrocyanins.

Example IV

Antiviral testing of F2a2 and F2a3 against human parainfluenza 3 virus (HPIV3) (FIG. 15) and influenza A/H3N2 (FIG. 16) was conducted. Influenza A/Sydney/05/97(H3N2) was used as a representative H3N2 strain. For F2a2 and HPIV3 (100 $TCID_{50}$), there was 100% inhibition at 100 mg/L, 75% inhibition at 10 mg/L, and no inhibition 1 mg/L and 0.1 mg/L. For F2a3 and HPFV3 (100 $TCID_{50}$), there was 100% inhibition at 100 mg/L, 75% inhibition at 10 mg/L, and no inhibition 1 mg/L and 0.1 mg/L. For F2a2 with H3N2 (100 $TCFD_{50}$), there was 100% inhibition at 100 mg/L, 33% inhibition at 10 mg/L, and no inhibition 1 mg/L and 0.1 mg/L. For F2a3 with H3N2 (100 $TCID_{50}$), there was 100% inhibition at 100 mg/L, and there was no inhibition 10 mg/L, 1 mg/L and 0.1 mg/L.

Example V

Characterization of F2a2 and F2a3 by UPLC-MS

In an attempt to identify the molecular source(s) of the anti-viral activity observed in cranberry juice extract, fractions F2a2 and F2a3, these fractions were analyzed by Ultra High Performance Liquid Chromatography (UPLC)-Quadrupole/Time Of Flight (Q-TOF) mass spectrometry (MS) or UPLC/Q-TOF MS for short. Diode array UV detection was also used in addition to MS.

UPLC Experimental Conditions
0.45 mL/min
A=0.1% Acetic Acid in Water
B=Acetonitrile
   Purge Solution=90/10 Water/Methanol
   Wash Solution=90/10 Methanol/Water
MS Experimental Conditions
Analysis of F2a2

Figure 17A:
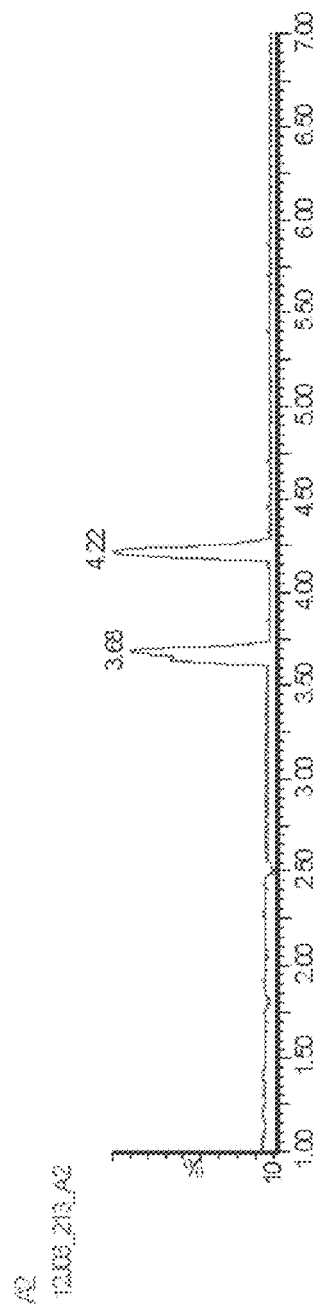
Figure 17B:
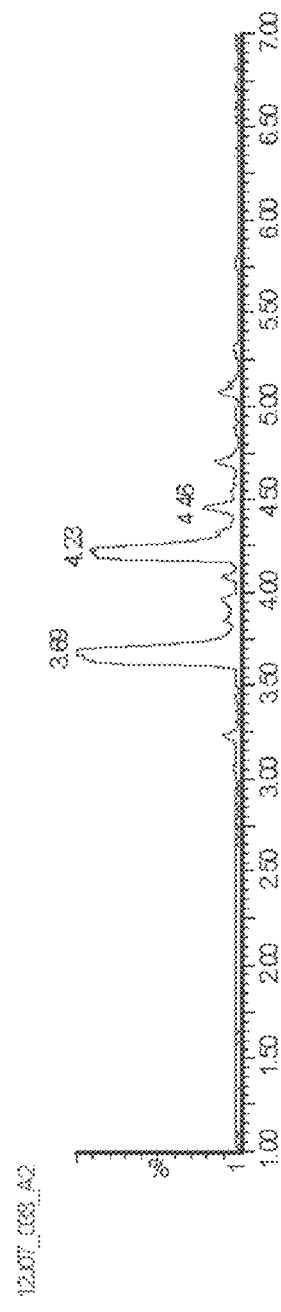

UPLC chromatograms of fraction F2a2 using positive ion MS detection (red), negative ion MS detection (green), and UV detection (purple) are shown in FIG. 17A. In all cases, two major peaks were observed at 3.68 min. and 4.22 min. The negative ion and UV traces also showed some additional minor components. These are highlighted in FIG. 17B, which is blowup of the baseline regions in each chromatogram. There are two main components of fraction F2a2 and one or both of these could be a source of the anti-viral activity observed in the material. It is also possible that one or more of the minor components of the material could be responsible for the antiviral activity. It is also possible that this particular combination of compounds is required for activity.

Figure 17C:
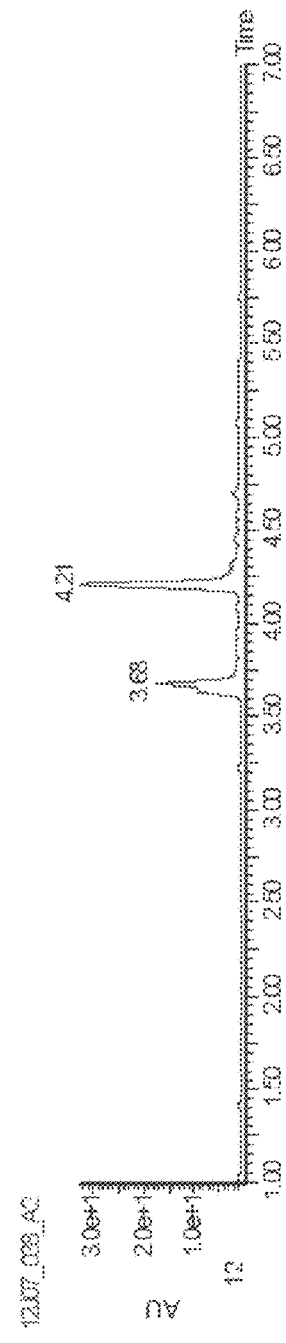
Figure 17D:
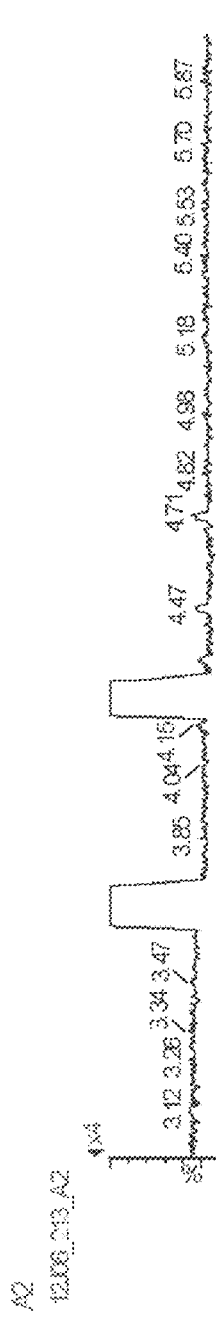
Figure 17E:
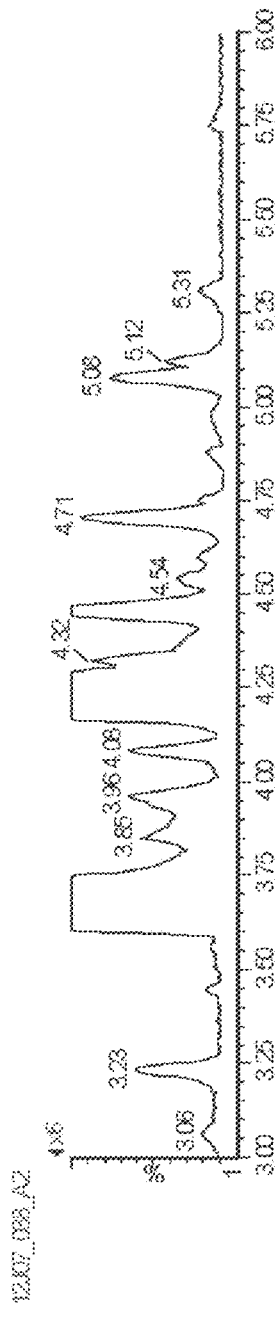
Figure 17F:
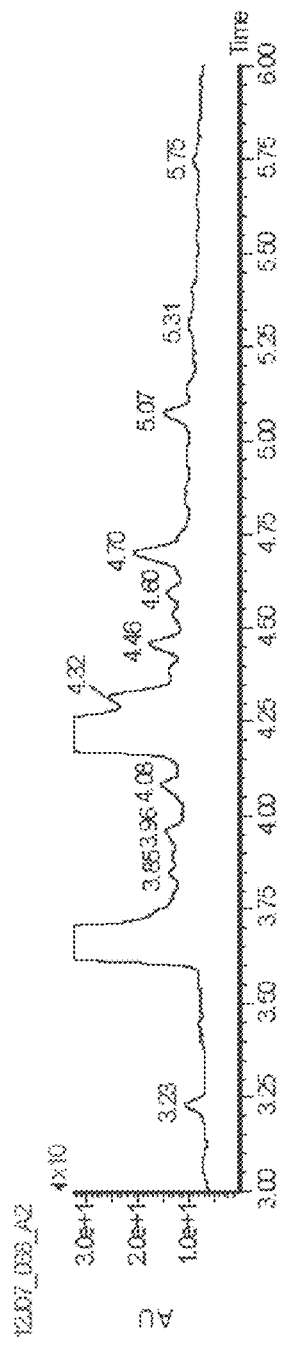
Figure 17G:
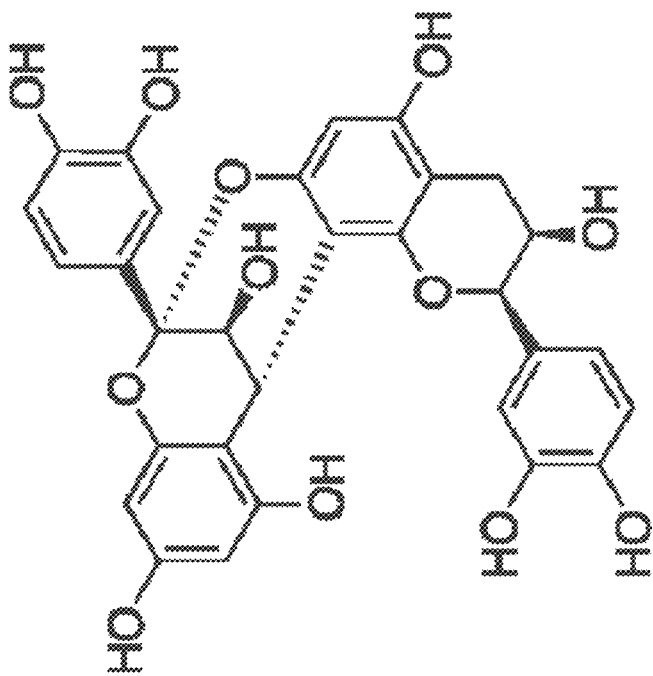
Figure 17G:
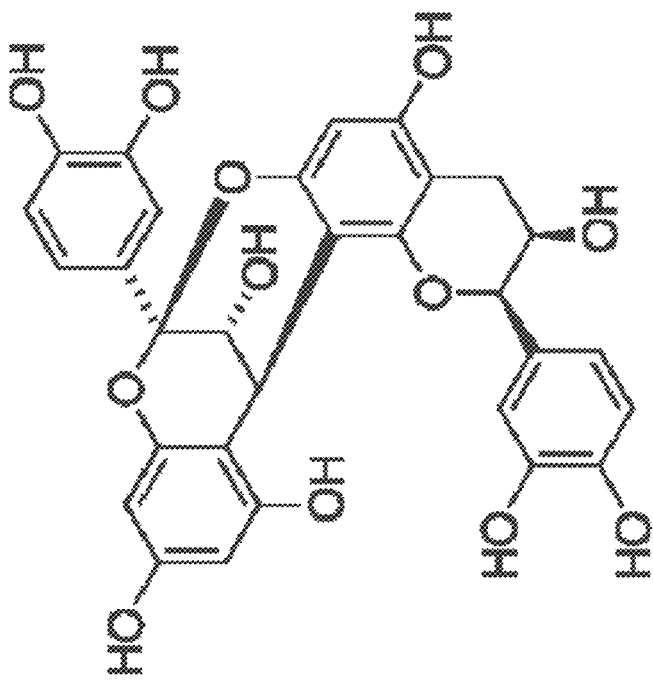

The molecular formulas of the peaks at 3.68 min. and 4.22 min. were determined by accurate mass analysis of molecular ion peaks. Both peaks were found to have molecular formula $C_{30}H_{24}O_{12}$ and have an average molecular weight of 576.50 amu. Hence, they are isomers of one another. Molecular fragmentation analysis was carried out on each of the two major components using tandem mass spectrometry. This data, combined with the molecular formula data gave structures for the peaks at 3.68 min. and 4.22 min., which are consistent with molecules from the proanthocyanidin A class of compounds. Examples of specific members of this class include proanthocyanidin A2 (also known as procyanidin A2) and proanthocyanidin A5' (also known as procyanidin A5'). Structures for these molecules are shown in FIG. 17C.

A general structure for the proanthocyanidin A class is shown below.

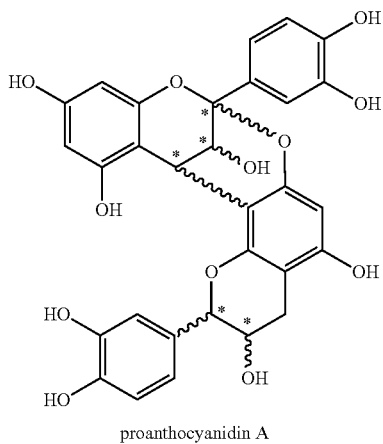 [SMILES: Oc1cc(O)c2c(c1)OC1(c3ccc(O)c(O)c3)Oc3cc(O)c4c(c3C2C1O)OC(c1ccc(O)c(O)c1)C(O)C4]

proanthocyanidin A

Members of the proanthocyanidin A class contain five stereogenic carbon atoms indicated by stars (*) in the figure above. Each stereogenic atom could be of either (R)- or (S)-configuration, leading to $2^5=32$ possible stereoisomers with varying combinations of (R)- and (S)-configurations at the starred atoms Those having common names are listed as follows, with Chemical Abstract Services (CAS) registry numbers in brackets and include proanthocyanidin A1 [103883-03-0], proanthocyanidin A2 [41743-41-3], proanthocyanidin A4 [111466-29-6], proanthocyanidin A5' [111466-30-9], proanthocyanidin A6 [114569-31-2], and proanthocyanidin A7 [114569-32-3], the structures of which are incorporated by reference herein Several other stereoisomers in the proanthocyanidin A class that do not have common names have also been described and are identified by their CAS numbers as [159247-90-2], [159247-88-8], [159247-85-5], [159247-89-9], [157086-14-1], [130853-74-6], [159247-85-5], and [135095-75-9], the structures of which are incorporated by reference herein. There are two known structural isomers of the proanthocyanidin A class that are consistent in both their molecular formula and in their fragmentation patterns with the compounds in fraction F2a2. These include the molecule pavetanin A [132651-90-2] and the compound with CAS number [201302-84-3], the structures of which are incorporated by reference herein.

Analysis of F2a3

Figure 18A:
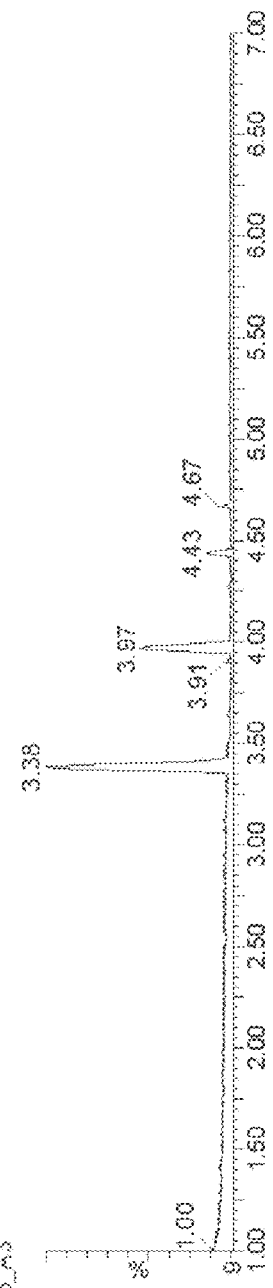
Figure 18B:
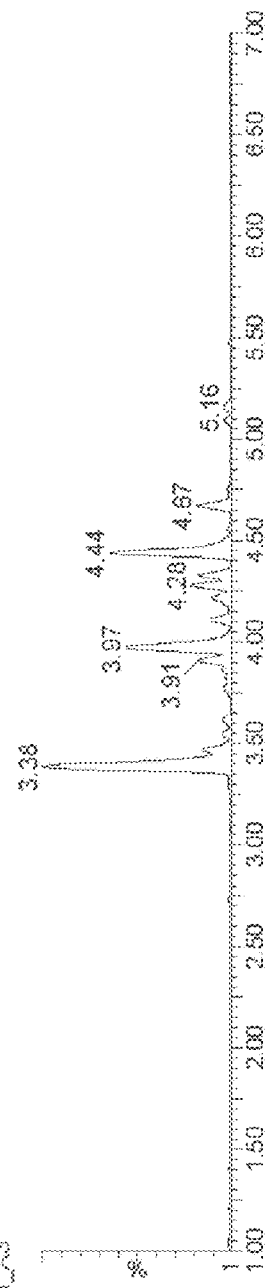
Figure 18C:
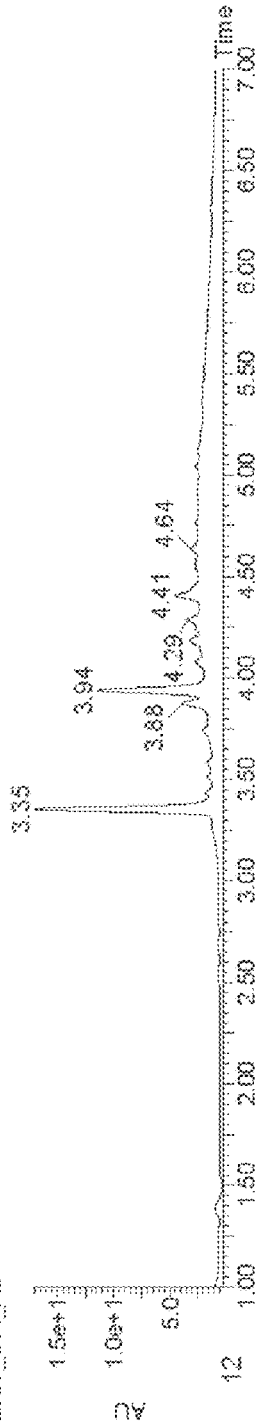
Figure 18D:
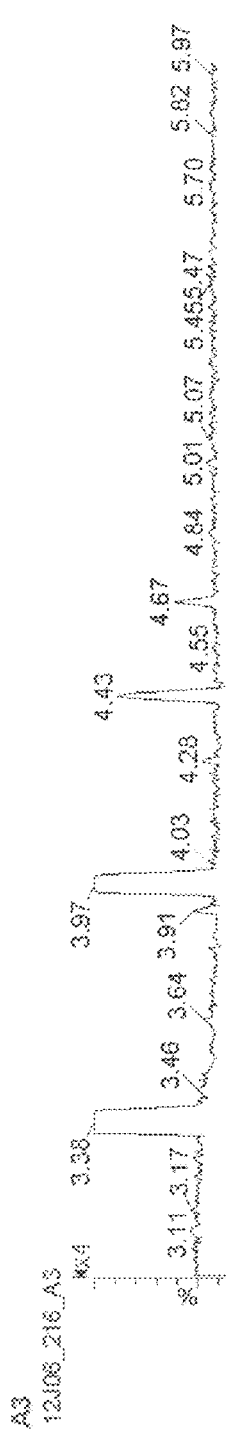
Figure 18E:
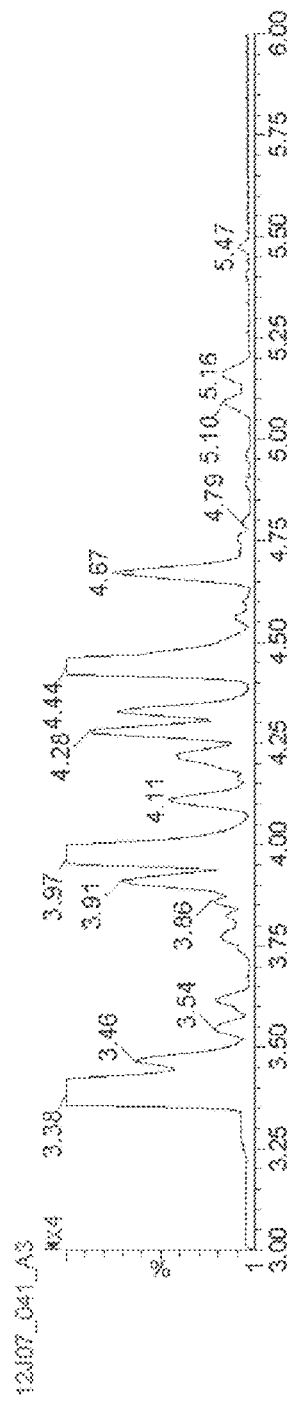
Figure 18F:
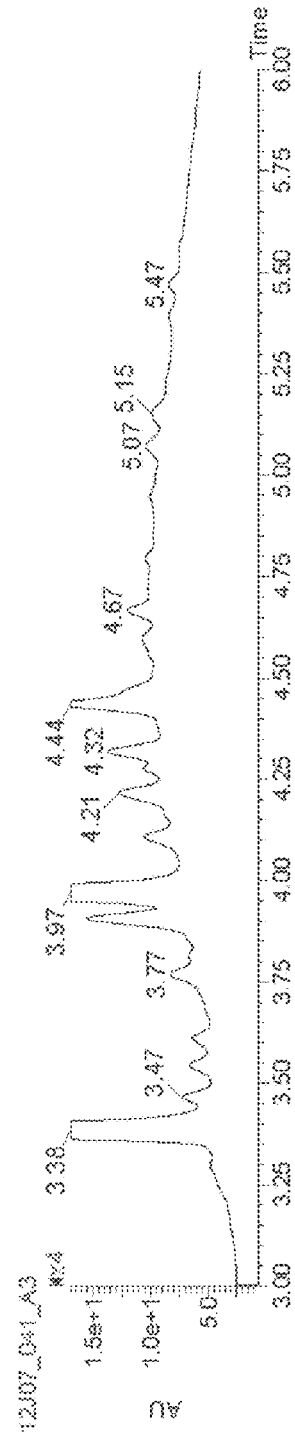
Figure 18G:
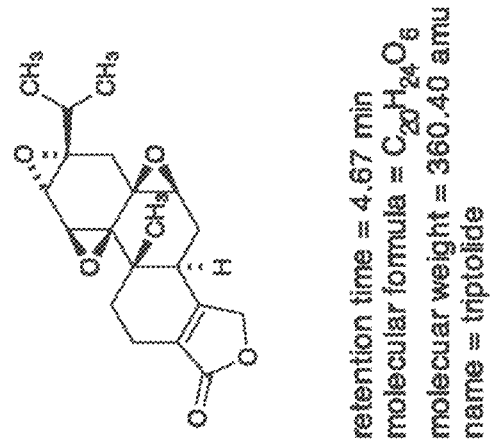
Figure 18G:
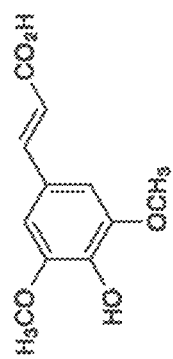
Figure 18G:
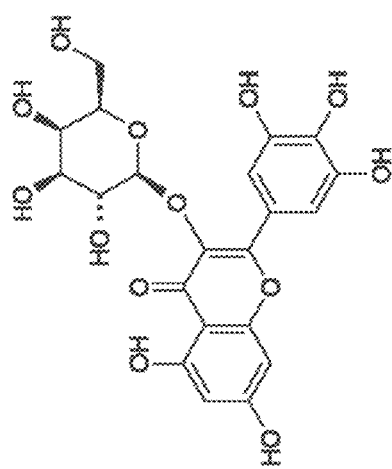

UPLC chromatograms of fraction F2a3 using positive ion MS detection (purple), negative ion MS detection (green), and UV detection (red) are shown in FIG. 18A. Two major peaks were observed at 3.38 min. and 3.97 min. in all chromatograms. Minor peaks at 4.44 min. and 4.67 min. were also observed. These are highlighted in FIG. 18B, which is blowup of the baseline regions in each chromatogram. It is also possible that any one or more of the major or minor components of the material could be responsible for the anti-viral activity. It is also possible that this particular combination of compounds is required for activity.

The molecular formulas of the peaks at 3.38 min., 3.97 min., 4.44 min., and 4.67 min, were determined by accurate mass analysis of molecular ion peaks. Additionally, molecular fragmentation analysis was carried out on each component using tandem mass spectrometry. This data, combined with the molecular formula data gave structures for the peaks at 3.38 min., 3.97 min., and 4.67 min., which are listed in FIG. 18C. The compound at 4.44 min had a molecular weight of 565.2287 amu. The best formula fit for this was $C_{28}H_{37}O_{12}$ Commercially available preparations of myricetin-beta-3-galactoside, procyanidin A2, sinapinic acid and triptolide were tested at various concentrations against vaccinia virus, herpes simplex virus-1, poliovirus Sabin-1, parainfluenza virus-3, and influenza A/California/July/2009 (H1N1). None of the compounds showed anti-viral activity at the concentrations tested (100 ng/mL-100 μg/mL and triptolide was toxic at 1-100 μg/mL).

The most time-consuming aspect of preparing fractions F2a2 and F2a3 is removing water solvent after chromatography separations. This has been done under reduced pressure with mild heating at 40° C. The process is significantly faster when heating at higher temperatures. However, it was unclear that the active compounds would be stable at higher temperatures. Therefore, a temperature stability study was undertaken comparing the anti vaccinia virus activities of materials prepared by evaporation at 40° C. 60° C., and 100° C. Materials were tested at stage one and two of the separation, leading to fractions F2 and F2a, respectively. The last step in the separation generates both F2a2 and F2a3.

Three samples of cranberry juice fractions F2 and F2a were prepared. Sample one was prepared using a rotary evaporation temperature of temperature of 40° C. throughout the procedure. The second sample was prepared using a rotary evaporation temperature of temperature of 60° C. throughout the procedure, and a third sample was prepared using a rotary evaporation temperature of temperature of 100° C. throughout the procedure. The samples were tested for stability of anti-viral activity against vaccinia virus (FIG.

19). The results are essentially identical for all three temperature points. This suggests that higher temperatures may be used during solvent evaporation without impacting anti-viral activity.

Example V

Characterization of Cranberry Seed Powder

To determine if cranberry seed extract can serve as an effective inhibitor when used to treat cells at various times after infection with vaccinia virus, vaccinia virus was added to ail test wells of BS-C-1 cells and incubated for one hour at 37° C., and then inhibitor was added to duplicate wells at 0 minutes, 30 minutes, one hour, and two hours post infection. The results (FIG. 20A) show that the inhibition is decreased when the inhibitor is added at times well after infection.

To determine if cranberry seed extract is a more or less effective inhibitor when cells are pretreated with it for various times prior to infection with vaccinia virus, 10 mg/L and 100 mg/L of the cranberry seed extracts were added to the test wells of BS-C-1 cells, and then virus was added to duplicate wells of each extract concentration after 0 minutes, one hour, two hours, and three hours. It appears that the most effective inhibition is obtained when the inhibitor is added within an hour of virus exposure.

Alternate extraction protocols were developed and tested for cranberry seed powder in an attempt to improve extract potency. Five different protocols were explored. In each, cranberry seed powder from Botanic Oil Innovations (5.000 g) was placed in a Soxhlet extraction apparatus. The following solvents were used: pure methanol, ethanol/water (95:5 v:v), isopropyl alcohol/water (88:12 v:v), n-propyl alcohol/water (72:28 v:v), and water. The extractions were run overnight and each solution was concentrated under reduced pressure, then lyophilized to a tan powder. Yields of solid extract ranged from 0.98 g (water) to 1.29 g (methanol). These materials were tested for anti-viral activity against vaccinia virus and influenza A/H1N1 (influenza A/California/July/2009).

Figure 21A:
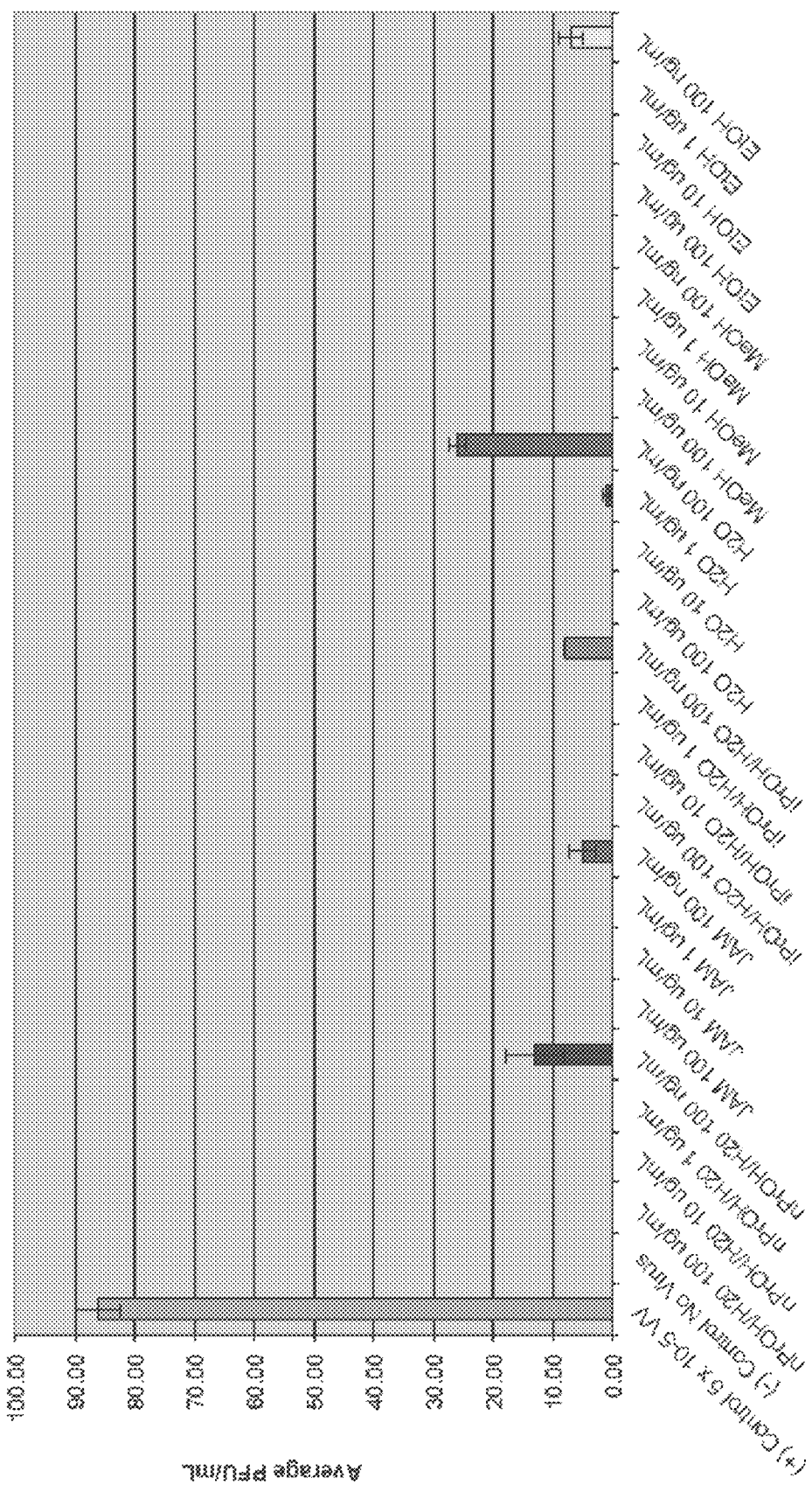
Figure 21C:
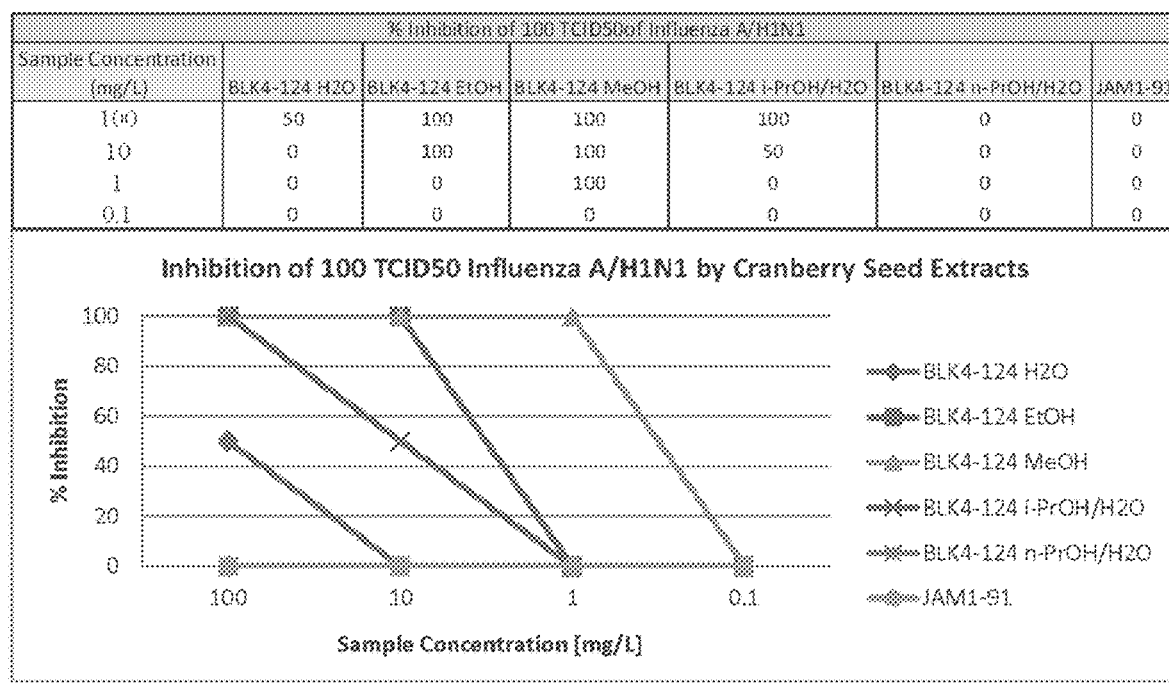
Figure 21D:
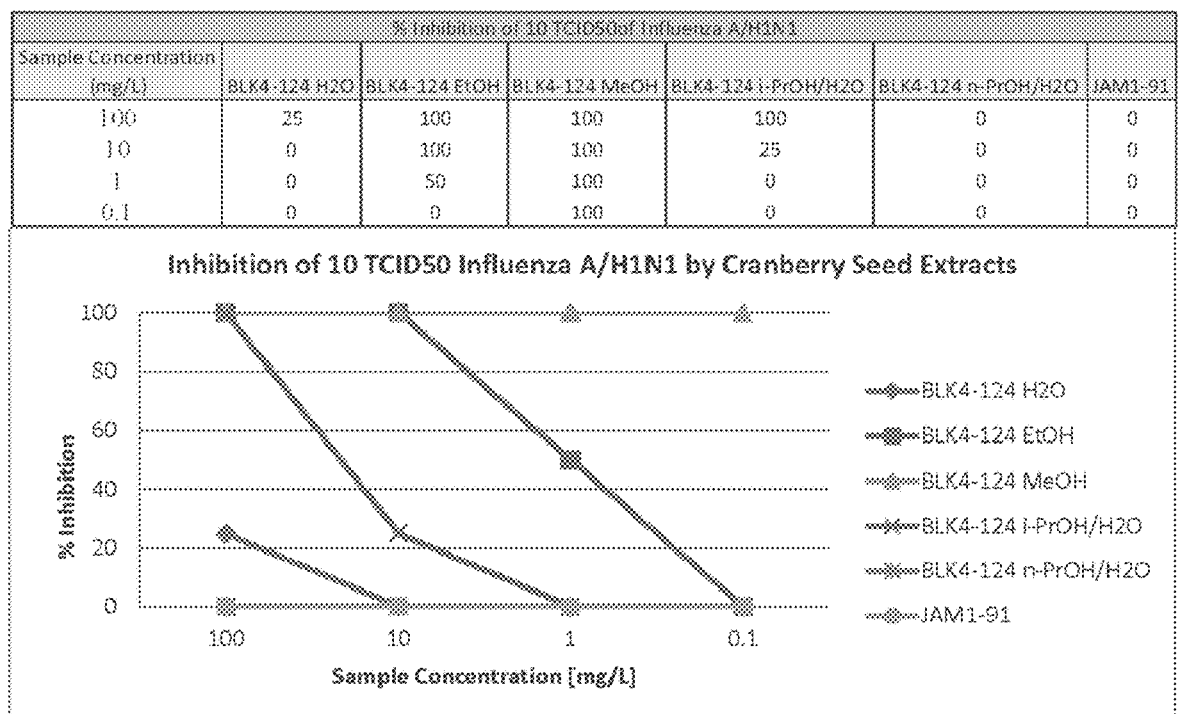

All of the materials tested were strong inhibitors of vaccinia virus (FIG. 21A). However, the material produced by methanol extraction (labeled MeOH) was the strongest inhibitor, and the material produced by water extraction (labeled as H$_2$O) was the weakest inhibitor.

For inhibition of 100 TCID$_{50}$ of influenza A/H1N1 with cranberry seed extracts, the methanol-derived material (MeOH) was by far the most potent inhibitor, followed by the ethanol-derived material (EtOH), the isopropyl alcohol/water material (i-PrOH/H$_2$O) and water materials. Materials derived from n-propyl alcohol/water or the previous extraction protocol (JAM1-91) showed no activity against 100 TCID$_{50}$ of influenza A/H1N1.

The anti-viral potency in inhibition of 10 TCID$_{50}$ of influenza A/H1N1 with cranberry seed extracts followed the same trend as the 100 TCID$_{50}$ results. In this case, the methanol-derived material inhibited 100% of the virus at ail concentrations tested.

REFERENCES

Tasaka, et al., JP 2013047196 A 20130307.
Lipson et al., Food and Environmental Virology (2012), 4(4), 168-178.
Theisen et al., Antiviral Research (2012), 94(2), 147-156.
Gallina et al., Antiviral Research (2011), 92(3), 447-452.
Gescher et al., Journal of Ethnopharmacology (2011), 134 (2), 468-474.
Gescher et al., Antiviral Research (2011), 89(1), 9-18.
Wu et al., Redai Yixue Zazhi (2010), 10(8), 1025-1028.
Xu et al., Journal of Agricultural and Food Chemistry (2010), 58(22), 11667-11672.
Su et al., Food Microbiology (2010), 27(8), 985-991.
Lee et al. U.S. Pat. Appl. Publ. (2010), US 20100168221 A1 20100701.
Su et al., Food Microbiology (2010), 27(4), 535-540.
Takeshita et al., U.S. Pat. Appl. Publ. (2010), US 20100055065 A1 20100304.
Iwasawa et al., Biocontrol Science (2009), 14(3), 107-111.
Takeshita et al., Journal of Biological Chemistry (2009), 284(32), 21165-21176.
Alberte et al., PCI Int. Appl. (2009), WO 2009026179 A2 2009022616.
Kappers et al., PCT Int, Appl. (2009), WO 2009020481 A2 20090212.
Iwasawa et al., JP 2008214297 A 20080918.
Ding et al., Zhongnan Yaoxue (2007), 5(2), 161-163. 19.
Yoshinaga et al., JP 2008143840 A 20080626.
Ghetea et al., Proceedings of SPIE (2008), 6991 (Biophotonics: Photonic Solutions for Better Health Care), 699128/1-699128/8.
Buzzini et al., Topics in Heterocyclic Chemistry (2007), 10 (Bioactive Heterocycles IV), 239-263.
Orhan et al., Chromatographia (2007), 66(Suppl.), S153-S157.
Yoshida et al., JP 2007217410 A 20070830.
Lipson et al., Molecular Nutrition & Food Research (2007), 51(6), 752-758.
Noda et al., WO 2006115123 A1 20061102.
Tokutake et al., JP 2005314316 A 20051110.
Weiss et al., US 20050196472 A1 20050908.
Matsumori et al., JP 2005239581 A 20050908.
Zhang et al., Quimica Nova (2005), 28(3), 421-425.
Maldonado et al., Journal of Agricultural and Food Chemistry (2005), 53(6), 1996-2001.
Cheng et al., Journal of the Science of Food and Agriculture (2005), 85(1), 10-15.
Kuo et. al., Journal of Pharmacy and Pharmacology (2004), 56(11), 1399-1406.
Cos et al., Current Medicinal Chemistry (2004), 11(10), 1345-1359.
Shahat et al., Planta Medica (2002), 68(6), 539-541.
Nakayama et al., JP 2002095916 A 20020402.
Lou et al., Current Topics in Phytochemistry (2000), 4, 79-93.
Lohezic et al., Pharmacy and Pharmacology Communications (1999), 5(3), 249-253.
Erdelmeier et al., Planta Medica (1996), 62(3), 241-245.
Ubillas et al., Phytomedicine (1994), 1(2), 77-106.
Tempesta et al., WO 9206695 A1 19920430.
Nonaka et al., WO 9004968 A1 19900517.
Balde et al., Phytotherapy Research (1990), 4(5), 182-8.
Lipson et al., Food and environmental virology (2012), 4(4), 168-78.
Ubillas et al., Phytomedicine: international journal of phytotherapy and phytopharmacology (1994), 1(2), 77-106.
Gallina et al., Antiviral research (2011), 92(3), 447-52.
Gescher et al., Journal of ethnopharmacology (2011), 134 (2), 468-74.
Gescher et al., Antiviral research (2011), 89(1), 9-18.
Xu et al., Journal of agricultural and food chemistry (2010), 58(22), 11667-72.
Su et al., Food microbiology (2010), 27(8), 985-91.

Iwasawa et al., Biocontrol science (2009), 14(3), 107-11.
Maldonado et al., Journal of agricultural and food chemistry (2005), 53(6), 1996-2001.
Kuo et al., The Journal of pharmacy and pharmacology (2004), 56(11), 1399-406.
Shahat et al., Planta medica (2002), 68(6), 539-41.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to isolate a plurality of compounds having anti-viral activity, comprising:
   a) providing a cranberry or cranberry seed extract dissolved or suspended in water, alcohol or in a water alcohol mixture;
   b) separating the extract on a C18 column into one or more fractions;
   c) separating the one or more fractions from the C18 column on a cationic ion exchange column, thereby providing one or more fractions from the cationic ion exchange column;
   d) separating the one or more fractions from the cationic ion exchange column on a C8 column into a plurality of fractions; and
   e) collecting one or more fractions from the C8 column having at least 80% by weight of a plurality of compounds that has anti-viral activity.

2. The method of claim 1, wherein the at least one fraction comprises about 1 mg to about 100 mg of the plurality of compounds with anti-viral activity.

3. The method of claim 1, further comprising subjecting the at least one isolated fraction to rotavapping at 40° C.

4. The method of claim 1, further comprising lyophilizing the at least one isolated fraction.

5. The method of claim 1, wherein the extract is a filtered extract.

6. The method of claim 1, wherein high pressure liquid chromatography is employed to separate the extract.

7. The method of claim 1, wherein the at least one isolated fraction has at least about 95% of the compounds with anti-viral activity.

8. The method of claim 1, wherein the extract is the cranberry extract.

9. The method of claim 1, wherein the extract is the cranberry seed extract.

10. The method of claim 1, further includes a plurality of chromatographic separation techniques are employed to isolate the at least one fraction in step e.

11. The method of claim 10, wherein the separation techniques include solid phase exchange, ion exchange chromatography, high performance liquid chromatography or simulated moving bed chromatography.

12. The method of claim 1, wherein the isolated at least one fraction contains a flavonol, proanthocyanin, diterpenoid epoxide, or phenylpropanoid.

* * * * *